US007235587B2

(12) United States Patent
Bonda et al.

(10) Patent No.: US 7,235,587 B2
(45) Date of Patent: Jun. 26, 2007

(54) DIESTERS CONTAINING TWO CRYLENE OR FLUORENE MOIETIES, SUNSCREEN COMPOSITIONS CONTAINING THE SAME, AND METHODS OF PHOTOSTABILIZING A SUNSCREEN COMPOSITIONS CONTAINING THE SAME

(75) Inventors: Craig A. Bonda, Winfield, IL (US); Anna B. Pavlovic, Elmwood Park, IL (US)

(73) Assignee: CPH Innovations Corporation, Chicago, IL (US)

( * ) Notice: Subject to any disclaimer, the term of this patent is extended or adjusted under 35 U.S.C. 154(b) by 543 days.

(21) Appl. No.: 10/883,507

(22) Filed: Jul. 1, 2004

(65) Prior Publication Data

US 2006/0002869 A1 Jan. 5, 2006

(51) Int. Cl.
*A61K 31/275* (2006.01)
*C07C 255/00* (2006.01)

(52) U.S. Cl. ...................................... 514/520; 558/402

(58) Field of Classification Search ..................... None
See application file for complete search history.

(56) References Cited

U.S. PATENT DOCUMENTS 3,215,724 A 11/1965 Strobel et al. .............. 260/465
3,215,725 A * 11/1965 Strobel et al. .............. 558/392
3,272,855 A 9/1966 Strobel et al. .............. 260/465
3,275,520 A 9/1966 Strobel et al. ............... 167/90
3,337,357 A 8/1967 Strobel et al. .............. 106/178
3,445,545 A 5/1969 Skoultchi .................... 260/881
3,461,108 A 8/1969 Heilman et al. ........... 260/78.5
3,560,455 A 2/1971 Hazen et al. ............... 526/272
3,560,456 A 2/1971 Hazen et al. ............... 526/272
3,560,457 A 2/1971 Hazen et al. ............... 526/272
3,580,893 A 5/1971 Heilman ..................... 525/384
3,706,704 A 12/1972 Heilman ..................... 526/208
3,729,450 A 4/1973 Galiano et al. ............. 528/500
3,729,451 A 4/1973 Blecke et al. .............. 260/78.5
3,860,700 A 1/1975 Viout et al. .................... 424/61
RE28,475 E 7/1975 Blecke et al. .............. 260/78.5
3,992,356 A 11/1976 Jacquet et al. ................ 260/47
4,069,046 A 1/1978 Hoegl et al. ...................... 96/1
4,107,290 A 8/1978 Jacquet et al. ................ 424/47
4,128,536 A 12/1978 Brodsky et al. .............. 427/54
4,178,303 A 12/1979 Lorenz et al. .............. 260/465
4,202,834 A 5/1980 Gruber et al. .............. 260/465
4,202,836 A 5/1980 Gruber et al. ........... 260/465.4
4,203,919 A 5/1980 Gruber et al. .............. 260/465
4,207,253 A 6/1980 Lorenz et al. .............. 260/465
4,218,392 A 8/1980 Lorenz et al. .............. 260/465
4,247,475 A 1/1981 Ching ........................ 260/465
4,260,719 A 4/1981 Ching ........................ 528/196
4,263,366 A 4/1981 Lorenz et al. .............. 428/332
4,264,680 A 4/1981 Anthony ..................... 428/412
4,276,136 A 6/1981 Gruber et al. .............. 204/159
4,387,089 A 6/1983 De Polo ...................... 424/59
4,489,057 A 12/1984 Welters et al. ................ 424/47
4,562,067 A 12/1985 Hopp et al. ................... 424/59
4,868,246 A 9/1989 MacLeay et al. ........... 525/142
5,013,777 A 5/1991 MacLeay et al. ........... 524/159
5,096,977 A 3/1992 MacLeay et al. ........... 525/343
5,210,275 A 5/1993 Sabatelli ...................... 560/43
5,321,112 A 6/1994 Olson .......................... 528/75
5,576,354 A 11/1996 Deflandre et al. .......... 514/685
5,681,871 A 10/1997 Molock et al. ............. 523/106
5,821,380 A 10/1998 Holderbaum et al. ....... 558/443
5,869,099 A 2/1999 Keller et al. ................ 424/486
5,882,633 A 3/1999 Pisson et al. ................. 424/59
5,972,324 A 10/1999 Zofchak et al. .......... 424/78.03
5,993,789 A 11/1999 Bonda et al. ................. 424/59
6,001,337 A 12/1999 Keller et al. .................. 424/59
6,033,649 A 3/2000 Gonzenbach et al. ......... 424/60
6,126,925 A 10/2000 Bonda et al. ................. 424/59
6,143,850 A 11/2000 Keller et al. ................ 526/304
6,224,854 B1 5/2001 Robinson ..................... 424/59
6,284,916 B1 9/2001 Bonda et al. ................. 560/80
6,297,300 B1 10/2001 Van Nuffel .................. 524/91

(Continued)

FOREIGN PATENT DOCUMENTS

CA 1 164 886 4/1984

(Continued)

OTHER PUBLICATIONS

"Photostability of HallStar Photostable SPF 32 Sunscreen Compared to Neutrogena UVA/UVB Sunblock SPF 30," Suncare Research Laboratories, Memphis, Tennessee (Oct. 5, 2000).

(Continued)

*Primary Examiner*—Paul A. Zucker
(74) *Attorney, Agent, or Firm*—Marshall, Gerstein & Borun LLP

(57) ABSTRACT

Diesters that include one or more of a crylene and/or a fluorene moiety, and sunscreen compositions including a mixture of a photoactive compound and one or more of a diester that includes one or more of a crylene and/or a fluorene moiety are described herein. Also disclosed are methods for stabilizing a sunscreen composition, methods of stabilizing a dibenzoylmethane derivative, and methods for protecting human skin from ultraviolet radiation with one or more of a diester that includes one or more of a crylene and/or a fluorene moiety are described herein.

80 Claims, 2 Drawing Sheets

U.S. PATENT DOCUMENTS

| | | | | |
|---|---|---|---|---|
| 6,306,507 | B1 | 10/2001 | Brunelle et al. | 428/423.7 |
| 6,358,892 | B1 | 3/2002 | Harrison et al. | 508/192 |
| 6,365,311 | B1 | 4/2002 | Wilson et al. | 430/108.2 |
| 6,416,773 | B2 | 7/2002 | Heidenfelder et al. | 424/401 |
| 6,441,071 | B1 | 8/2002 | Van Nuffel | 524/316 |
| 6,485,713 | B1 | 11/2002 | Bonda et al. | 424/59 |
| 6,491,901 | B2 | 12/2002 | Gers-Barlag et al. | 424/59 |
| 6,544,305 | B2 | 4/2003 | Wood et al. | 44/275 |
| 6,610,409 | B2 | 8/2003 | Pickett et al. | 428/423.7 |
| 6,689,474 | B2 | 2/2004 | Pickett et al. | 428/423.7 |
| 2001/0022966 | A1 | 9/2001 | Gers-barlag et al. | 424/59 |
| 2002/0194777 | A1 | 12/2002 | Wood et al. | 44/275 |
| 2003/0000130 | A1 | 1/2003 | Wood et al. | 44/275 |
| 2003/0069338 | A1 | 4/2003 | Goossens et al. | 524/186 |
| 2003/0072945 | A1 | 4/2003 | Pickett et al. | 428/412 |
| 2003/0130390 | A1 | 7/2003 | Gorny et al. | 524/307 |
| 2003/0180542 | A1 | 9/2003 | Pickett et al. | 428/423.7 |
| 2004/0057912 | A1 | 3/2004 | Bonda et al. | 424/59 |

FOREIGN PATENT DOCUMENTS

| | | |
|---|---|---|
| CA | 2204430 | 5/1996 |
| DE | 31 06 071 | 2/1982 |
| DE | 44 40 055 | 5/1996 |
| DE | 195 19 895 | 12/1996 |
| DE | 196 30 479 | 1/1998 |
| DE | 10008895 | 8/2001 |
| DE | 100 15 863 | 10/2001 |
| DE | 100 26 628 | 12/2001 |
| DE | 100 58 290 | 5/2002 |
| EP | 0 675 875 | 11/1998 |
| EP | 0 900 782 | 3/1999 |
| EP | 1129696 | 9/2001 |
| EP | 1 308 084 | 5/2003 |
| GB | 1129029 | 10/1968 |
| JP | 56-140959 | 4/1981 |
| JP | 8-262759 | 10/1996 |
| JP | 11-143095 | 5/1999 |
| WO | WO 94/14760 | 7/1994 |
| WO | WO 96/15102 | 5/1996 |
| WO | WO 00/44340 | 8/2000 |
| WO | WO 01/16224 | 3/2001 |
| WO | WO 01/57125 | 8/2001 |
| WO | WO 01/90233 | 11/2001 |
| WO | WO 01/92395 | 12/2001 |
| WO | WO 02/42368 | 5/2002 |
| WO | WO 2004/031294 | 4/2004 |

OTHER PUBLICATIONS

Beckwith, in "The chemistry of amides: Synthesis of amides," Zabicky, J., Ed. Interscience: New York, pp. 73-185 (1970).

Bentley et al., "Medium Effects on the Rates and Mechanisms of Solvolytic Reactions," *Adv. Phys. Org. Chem.*, vol. 14, pp. 1-67 (1977).

Bentley et al., "$Y_X$ Scales of Solvent Ionizing Power," *Progr. Phys. Org. Chem.*, vol. 17, pp. 121-158 (1990).

Dimroth et al., Über Pyridinium-*N*-Phenol-Betaine Und Ihre Ver Wendung Zur Charakterisierung Der Polarität. Von LöSungsmitteln *Justus Liebigs Ann. Chem.*, vol. 661 pp. 1-37 (1963).

Fainberg et al., "Correlation of Solvolysis Rates. III. *t*-Butyl Chloride in a Wide Range of Solvent Mixtures," *J. Am Chem. Soc.*, vol. 78 pp. 2770-2777 (1956).

Grunwald et al., "The Correlation of Solvolysis Rates," J. Am. Chem. Soc., vol. 70, pp. 846-854 (1948).

Haslem, "Recent Developments in Methods For the Esterification and Protection of the Carboxyl Group," *Tetrahedron*, vol. 36, pp. 2409-2433 (1980).

Kamlet et al., "An Examination of Linear Solvation Energy Relationships," *Progr. Phys. Org. Chem.*, vol. 13, pp. 485-630 (1981).

Kosower, "The Effect of Solvent on Spectra. I. A New Empirical Measure of Solvent Polarity Z-Values," *J. Am Chem. Soc.*, vol. 80, pp. 3253-3260 (1958).

McNaught et al., "IUPAC Compendium of Chemical Terminology," 2nd Ed. (1997).

Reichardt, "Solvents and Solvent Effects in Organic Chemistry," 2nd Ed., Chap. 7: Empirical Parameters of Solvent Polarity, VCH Publishers, New York, New York (1998).

Sayre et al., "Photostability Testing of Avobenzone," Allured's Cosmetics & Toiletries Magazine, vol. 114, No. 5, pp. 85-91 (May 1999).

Tarras-Wahlberg et al., "Changes in Ultraviolet Absorption of Sunscreens After Ultraviolet Radiation," *J. Investigative Dermatology*, vol. 113, No. 4, pp. 547-553 (1999).

Turro, *Modern Molecular Photochemistry* Benjamin/Cummings Publ. Co., Menlo Park, California, pp. 296-361 (1991).

Bettencourt et al., "Kinetics of proton transfer from phosphonium ions to electrogenerated basis: polar, steric and structural influences on kinetic acidity and basicity" *J. Chem. Soc., Perkin Trans.* 2, pp. 515-522 (1998).

Lehnert, Knoevenagel-Kondensationen Mit $TiC1_4$ /BASE-III[1] Tetrahedron vol. 29, pp. 635-638 (1973).

Wittig et al., "zur Umkehrbarkeit von Kondensationsrektionen in alkalischen Medium", Chemische Berichte, p. 117, lines 13-21, vol. 83 (1950).

* cited by examiner

DIESTERS CONTAINING TWO CRYLENE OR FLUORENE MOIETIES, SUNSCREEN COMPOSITIONS CONTAINING THE SAME, AND METHODS OF PHOTOSTABILIZING A SUNSCREEN COMPOSITIONS CONTAINING THE SAME

BACKGROUND OF THE INVENTION

Field of the Invention

The invention relates to compounds, compositions, and methods to increase the photostability of a sunscreen composition. More particularly, the invention relates to diesters that include two one or more of a crylene moiety ((2E)-2-cyano-3,3-diphenylprop-2-enoic acid) and/or a fluorene moiety (2-cyano-2-fluoren-9-ylideneacetic acid), and methods of using such compounds.

BRIEF DESCRIPTION OF RELATED TECHNOLOGY

It is well known that ultraviolet radiation (light) having a wavelength from about 280 nm or 290 nm to about 320 nm (UV-B) is harmful to human skin, causing burns that are detrimental to the development of a good sun tan. UV-A radiation (about 320 nm to about 400 nm), while producing tanning of the skin, also can cause damage, particularly to very lightly-colored or sensitive skin, leading to reduction of skin elasticity and wrinkles. Therefore, a sunscreen composition for use on human skin preferably includes both a UV-A and a UV-B filter to prevent most of the sunlight within the full range of about 280 nm or 290 nm to about 400 nm from damaging human skin.

Ultraviolet radiation from the sun or artificial sources can also cause harm to coatings containing photoactive substances, such as photoactive pigments and dyes, by breaking down chemical bonds in the structure of a component such as a polymer, a pigment, or a dye. This photodegradation can lead to color fading, loss of gloss, and loss of physical and protective properties of a coating. Photodegradation can take place in several steps which include one or more components of a coating absorbing UV radiation. The absorbed radiation can excite the absorbing molecules and raise them to a higher energy level, which can be very reactive. If the molecule cannot be relaxed, bond cleavage and the formation of free radicals will occur. These free radicals can attack one or more color molecules and/or a polymer backbone and form more free radicals. UV-A and UV-B filters can also be used to absorb UV radiation to protect a pigmented coating.

The UV-B filters that are most widely used in the U.S. in commercial sunscreen compositions are paramethoxycinnamic acid esters, such as 2-ethylhexyl paramethoxycinnamate, commonly referred to as octyl methoxycinnamate or PARSOL MCX, octyl salicylate, and oxybenzone.

The organic UV-A filters most commonly used in commercial sunscreen compositions are the dibenzoylmethane derivatives, particularly 4-(1,1-dimethylethyl)-4'-methoxydibenzoylmethane (also called avobenzone, sold under the brand name PARSOL 1789). Other dibenzoylmethane derivatives described as UV-A filters are disclosed in U.S. Pat. Nos. 4,489,057, 4,387,089 and 4,562,067, the disclosures of which are hereby incorporated herein by reference. It is also well known that the above described UV-A filters, particularly the dibenzoylmethane derivatives, can suffer from rapid photochemical degradation, when used alone or when combined with the above-described most commercially used UV-B filters.

Typically, the above-described UV-B filters are combined with the above described UV-A filters in a solution with other lipophilic or oily ingredients. This solution of oily ingredients, known to formulators of cosmetic products including sunscreens as the "oil phase," is typically, but not necessarily, dispersed with the help of emulsifiers and stabilizers into an aqueous solution composed primarily of water, to make an emulsion which becomes a final cream or lotion form of a sunscreen composition.

The performance of a photoactive compound or a combination of photoactive compounds in a sunscreen composition has been extremely difficult to predict based on the levels of photoactive compounds in the formulation, particularly when the formulation includes one or more photoactive compounds that suffer from relatively rapid photodegradation, such as avobenzone. Because of this, each formulation has required expensive laboratory testing to determine the UV absorbance, as a function of time (quantity) of exposure of the formulation to UV radiation. Moreover, a particularly difficult problem is presented when one photoactive compound in a sunscreen composition acts to increase the rate of photodegradation of another photoactive compound in the composition. This can be accomplished in a number or ways, including a bimolecular reaction between two photoactive compounds and a lowering of the threshold energy need to raise a photoactive compound to its excited state. For example, when avobenzone is combined with octyl methoxycinnamate a bimolecular pathway leads to the rapid photodegradation of both the dibenzoylmethane derivative and the octyl methoxycinnamate.

Methods and compositions for stabilizing photoactive compounds, such as dibenzoylmethane derivatives with the use of diesters and/or a polyesters of naphthalene dicarboxylic acid are described in U.S. Pat. Nos. 5,993,789, and 6,284,916, the disclosures of which are hereby incorporated herein by reference. Other methods of stabilizing a dibenzoylmethane derivative include the addition of an α-cyano-β,β-diphenylacrylate compound to a sunscreen composition including a dibenzoylmethane derivative. See, Deflandre et al, U.S. Pat. No. 5,576,354 and Gonzenbach et al., U.S. Pat. No. 6,033,649.

SUMMARY

Figure 1:
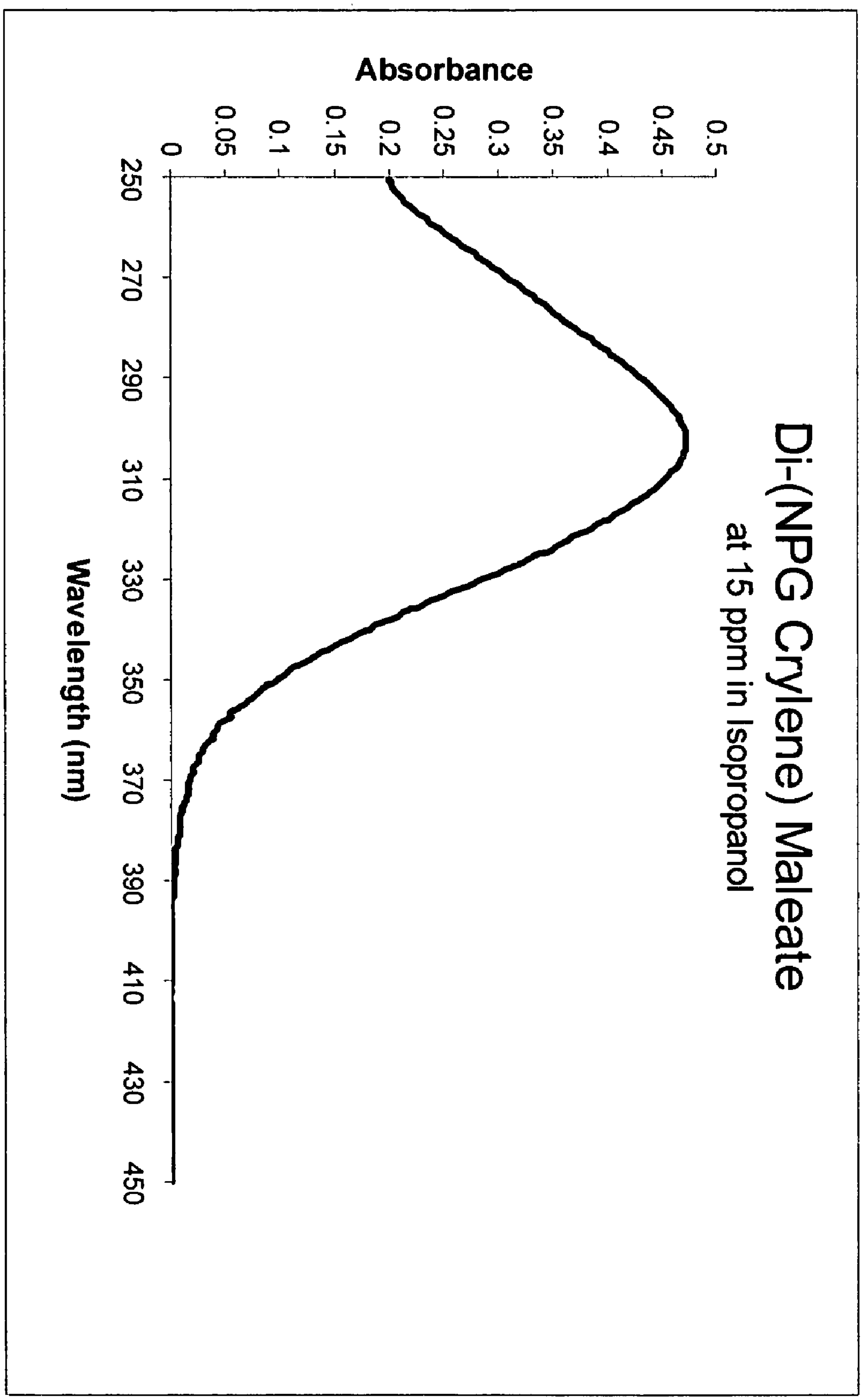
FIG. 1 is a graph of the absorbance of the Di(NPG Crylene) Maleate UV-absorbing compound, from a wavelength of 250 nm to 450 nm, and at a concentration of 15 ppm (parts per million) in isopropanol.

One aspect of the compounds, compositions, and methods disclosed herein includes a diester that includes two crylene moieties.

Another aspect of the compounds, compositions, and methods disclosed herein includes a diester that includes two fluorene moieties.

Another aspect of the compounds, compositions, and methods disclosed herein includes a diester that includes one crylene moiety and one fluorene moiety.

Another aspect of the compounds, compositions, and methods disclosed herein includes one or more of a diester that includes two crylene moieties, a diester that includes two fluorene moieties and/or a diester that includes one crylene moiety and one fluorene moiety.

Another aspect of the compounds, compositions, and methods disclosed herein includes a method for stabilizing a dibenzoylmethane derivative by the addition of one or more of a diester that includes two crylene moieties, a diester that includes two fluorene moieties and/or a diester that includes one crylene moiety and one fluorene moiety.

Another aspect of the compounds, compositions, and methods disclosed herein is a sunscreen composition that includes one or more of a diester that includes two crylene moieties, a diester that includes two fluorene moieties and/or a diester that includes one crylene moiety and one fluorene moiety.

Another aspect of the compounds, compositions, and methods disclosed herein includes a method for stabilizing a sunscreen composition including a photoactive compound by the addition of a photostabilizing amount of one or more of a diester that includes two crylene moieties, a diester that includes two fluorene moieties and/or a diester that includes one crylene moiety and one fluorene moiety.

Another aspect of the compounds, compositions, and methods disclosed herein includes a method of protecting human skin from ultraviolet radiation including the steps of applying to the skin, one or more of a diester that includes two crylene moieties, a diester that includes two fluorene moieties and/or a diester that includes one crylene moiety and one fluorene moiety.

Another aspect of the compounds, compositions, and methods disclosed herein includes a fumarate diester that includes two crylene moieties.

Another aspect of the compounds, compositions, and methods disclosed herein includes a maleate diester that includes two crylene moieties.

Another aspect of the compounds, compositions, and methods disclosed herein includes a fumarate diester that includes two fluorene moieties.

Another aspect of the compounds, compositions, and methods disclosed herein includes a maleate diester that includes two fluorene moieties.

Another aspect of the compounds, compositions, and methods disclosed herein includes a sunscreen composition that includes one or more of a fumarate diester that includes two crylene moieties, a maleate diester that includes two crylene moieties, a fumarate diester that includes two fluorene moieties and/or a maleate diester that includes two fluorene moieties.

Still another aspect of the compounds, compositions, and methods disclosed herein includes a method for stabilizing a sunscreen composition including a photoactive compound by the addition of a photostabilizing amount of one or more of a fumarate diester that includes two crylene moieties, a maleate diester that includes two crylene moieties, a fumarate diester that includes two fluorene moieties and/or a maleate diester that includes two fluorene moieties.

Still another aspect of the compounds, compositions, and methods disclosed herein is a method for stabilizing a sunscreen composition including a photoactive compound by the addition of a photostabilizing amount of one or more of a fumarate ester derivative that includes two crylene moieties and/or a maleate ester derivatives that include two crylene moieties.

Another aspect of the compounds, compositions, and methods disclosed herein is a method for stabilizing a dibenzoylmethane derivative by the addition of one or more of a fumarate diester that includes two crylene moieties, a maleate diester that includes two crylene moieties, a fumarate diester that includes two fluorene moieties and/or a maleate diester that includes two fluorene moieties.

Still another aspect of the compounds, compositions, and methods disclosed herein is a method of protecting human skin from ultraviolet radiation including the steps of applying to the skin, one or more of a fumarate diester that includes two crylene moieties, a maleate diester that includes two crylene moieties, a fumarate diester that includes two fluorene moieties and/or a maleate diester that includes two fluorene moieties.

DETAILED DESCRIPTION OF THE PREFERRED EMBODIMENTS

Sunscreen compositions typically include one or more photoactive compounds that can absorb UV radiation, and often sunscreen compositions include a variety of photoactive compounds to absorb UV-radiation over the entire UV range (UV-A and UV-B range). Diesters that include crylene and fluorene moieties, compositions that include diesters that include crylene and fluorene moieties, and methods of use of such compounds are described herein.

The general structure of a crylene moiety ((2E)-2-cyano-3,3-diphenylprop-2-enoic acid) is shown below:

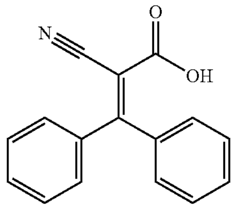

Optionally, each of the aromatic rings on the core crylene moiety can be substituted with various functional groups.

The general structure of a fluorene moiety (2-cyano-2-fluoren-9-ylideneacetic acid) is shown below:

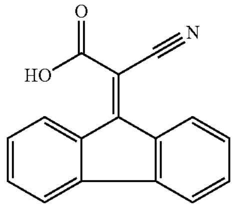

Optionally, each of the aromatic rings on the core fluorene moiety can be substituted with various functional groups.

It has been found that diesters that include one or more of a crylene and/or a fluorene moiety, are capable of absorbing and/or dissipating UV radiation, as well as photostabilizing another UV-absorbing compound. Nonlimiting example of such compounds are shown below:

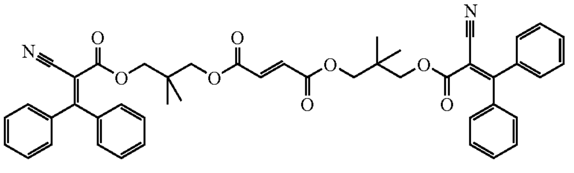

Di (NPG Crylene) Fumarate

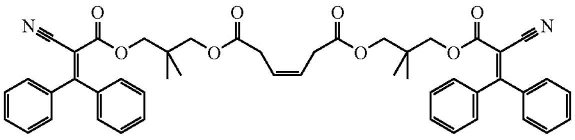

Di (NPG Crylene) Maleate

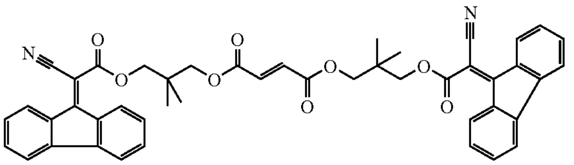

Di (NPG Fluorene) Fumarate

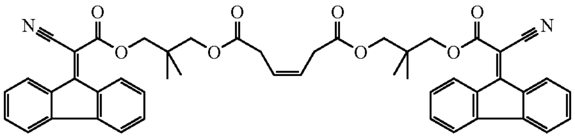

Di (NPG Fluorene) Maleate

For ease of reference, the compound shown above shall be referred to by their short-hand names as labeled above (e.g., Di(NPG Crylene)) rather than by their formal IUPAC names (e.g., 3-((2E)-2-cyano-3,3-diphenylprop-2-enoyloxy)-2,2-dimethylpropyl 4-((2Z)-2-cyano-3,3-diphenylprop-2-enoyloxy)-2,2-dimethylbutyl (2E)but-2-ene-1,4-dioate).)

Sunscreen compositions containing one or more photoactive compounds, such as a dibenzoylmethane derivative UV-A filter compound, and one or more of a diester that includes two crylene moieties (e.g., Di(NPG Crylene) Fumarate), a diester that includes two fluorene moieties (e.g., Di(NPG Fluorene) Maleate), and/or a diester that includes one crylene moiety and one fluorene moiety. One aspect of the sunscreen compositions described herein are methods of photostabilizing a sunscreen composition including a dibenzoylmethane derivative, such as 4-(1,1-dimethylethyl)-4'-methoxydibenzoylmethane (PARSOL® 1789), wherein one or more photoactive compounds present in a sunscreen composition (e.g., avobenzone) are made more photostable by the addition of one or more of a diester that includes two crylene moieties (e.g., Di(NPG Crylene) Maleate), a diester that includes two fluorene moieties (e.g., Di(NPG Fluorene) Maleate), and/or a diester that includes one crylene moiety and one fluorene moiety. Also disclosed herein are methods for filtering out ultra-violet light from human skin including the step of applying one or more of a diester that includes two crylene moieties (e.g., Di(NPG Crylene) Maleate), a diester that includes two fluorene moieties (e.g., Di(NPG Fluorene) Maleate), and/or a diester that includes one crylene moiety and one fluorene moiety.

A photoactive compound can be considered stable when, for example, after 30 MED irradiation the photoactive compound has retained at least about 90% of its original absorbance at a wavelength or a range of wavelengths of interest (e.g., the wavelength at which or near a photoactive compound has a peak absorbance, such as 350-370 nm for avobenzone). Likewise, a sunscreen composition can include a plurality of photoactive compounds and a sunscreen composition, as a whole, can be considered stable when, for example, after 30 MED irradiation the sunscreen composition has retained at least about 90% of its original absorbance at one or more wavelengths of interest (e.g., at or near the peak absorbance wavelength of the primary photoactive compounds).

It has surprisingly been found that the addition of one or more of a diester that includes two crylene moieties (e.g., Di(NPG Crylene) Maleate), a diester that includes two fluorene moieties (e.g., Di(NPG Fluorene) Maleate), and/or a diester that includes one crylene moiety and one fluorene moiety to a sunscreen composition including a diester or polyester of naphthalene dicarboxylic acid can significantly increase the photostability of the sunscreen composition and/or photounstable components present therein. Without intending to be limited to any particular mechanism of achieving this increase in stability, it is believed that a diester or polyester of naphthalene dicarboxylic acid stabilizes a dibenzoylmethane derivative by accepting the triplet energy of the dibenzoylmethane derivative once the dibenzoylmethane derivative has reached an excited state as a result of the absorption of ultra-violet light. Once a dibenzoylmethane derivative is excited, it is prone to degrade according to a number of pathways; however, the degradation of the dibenzoylmethane derivative can be substantially reduced or prevented by the use of a diester or polyester of naphthalene dicarboxylic acid to quench (accept) the triplet excited state energy present in an excited dibenzoylmethane molecule. Thus, in one pathway of degradation, a dibenzoylmethane derivative is excited to its triplet state and the excited state triplet energy is released in a bond breaking step, thereby preventing the dibenzoylmethane derivative from further accepting ultra-violet radiation. A diester or polyester of naphthalene dicarboxylic acid may stabilize a dibenzoylmethane derivative by accepting the triplet state (excited state) energy of the excited dibenzoylmethane derivative in such a way as to convert the excited dibenzoylmethane derivative back to a ground state that is capable of reaccepting ultra-violet radiation (energy transfer). See Bonda et al., U.S. Pat. Nos. 6,113,931, 6,284,916, 6,518,451, and 6,551,605, the disclosures of which are hereby incorporated by reference.

For this process to work continuously, the diester or polyester of naphthalene dicarboxylic acid must transfer or convert the energy that was accepted from the excited dibenzoylmethane derivative. Without intending to be limited to a particular mechanism, it is believed that when a diester or polyester of naphthalene dicarboxylic acid is excited to its triplet state it dissipates the triplet excited state energy through vibrations (e.g., as heat), which in this group of molecules is a relatively slow mode of dissipating energy. It has been found, quite surprisingly, that by the addition of one or more of a diester that includes two crylene moieties (e.g., Di(NPG Crylene) Maleate), a diester that includes two fluorene moieties (e.g., Di(NPG Fluorene) Maleate), and/or a diester that includes one crylene moiety and one fluorene moiety to a composition that includes a diester or polyester of naphthalene dicarboxylic acid, such compounds are able to accept triplet excited state energy from an excited diester or polyester of naphthalene dicarboxylic acid. Thus, according to one possible mechanism, the efficiency of the dissipation of the excited state energy in an excited diester or polyester of naphthalene dicarboxylic acid is greatly improved by a transfer of energy from an excited diester or polyester of naphthalene dicarboxylic acid to a diester described herein.

Thus, preferably, a sunscreen composition disclosed herein includes one or more of a diester that includes two crylene moieties (e.g., Di(NPG Crylene) Maleate), a diester that includes two fluorene moieties (e.g., Di(NPG Fluorene) Maleate), and/or a diester that includes one crylene moiety and one fluorene moiety and a diester or polyester of naphthalene dicarboxylic acid selected from the group consisting of compounds of formulae (XX) and (XXI), and combinations thereof:

(XX)

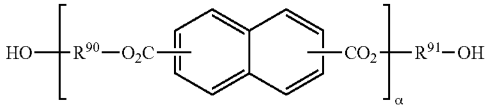

(XXI)

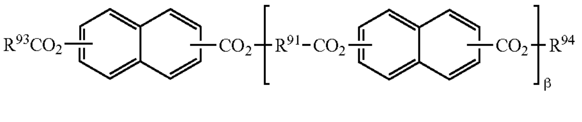

wherein $R^{93}$ and $R^{94}$ are the same or different and selected from the group consisting of $C_1$-$C_{22}$ alkyl groups, diols having the structure HO—$R^{91}$—OH and polyglycols having the structure HO—$R^{90}$—(—O—$R^{91}$—)$_\gamma$—OH; wherein each $R^{90}$ and $R^{91}$ is the same or different and selected from the group consisting of $C_1$-$C_6$ straight or branched chain alkyl groups; and wherein α and γ are each in a range of 1 to 100 and β is in a range of 0 to 100. Preferably, the UV-absorbing compositions disclosed herein include a diester or polyester of naphthalene dicarboxylic acid in a range of about 0.1% to about 15% by weight of the total weight of the composition.

A sunscreen composition disclosed herein can be combined into a cosmetically acceptable carrier, optionally including emollients, stabilizers, emulsifiers, such as those known in the art, and combinations thereof. These additives can be used in preparing an emulsion from an aqueous system and a mixture of a filter system that includes one or more photoactive compounds and a solvent system that includes one or more organic solvents. When made, preferably the emulsion is an oil-in-water emulsion, wherein the oil phase is primarily formed from a mixture of the filter system and solvent system.

A typical sunscreen composition includes one or more photoactive compounds, wherein a photoactive compound acts to absorb UV radiation and thereby protect the substrate (e.g., human skin) from the harmful effects of UV radiation. The absorption process causes a photoactive compound to reach an excited state, wherein the excited state is characterized by the presence of excited energy (e.g., singlet energy or triplet energy), as compared to the ground state of the photoactive compound. Once a photoactive compound reaches an excited state there exists a number of pathways by which the excited photoactive compound can dissipate its excess energy (e.g., triplet energy), however, many of those pathways adversely affect the ability of the photoactive compound to further absorb UV radiation.

It has surprisingly been found that the addition of one or more of a diester that includes one or more crylene moieties (e.g., Di(NPG Crylene) Maleate) increases the photostability of a sunscreen composition. Without intending to be limited to any particular mechanism by which a such compounds are able to quench (accept the excited state energy) an excited photoactive compound, it is believed that diesters containing one or more of a crylene moiety accept the excited state energy and dissipates the energy kinetically in the form of rapid isomerizations. An example of this process is shown below:

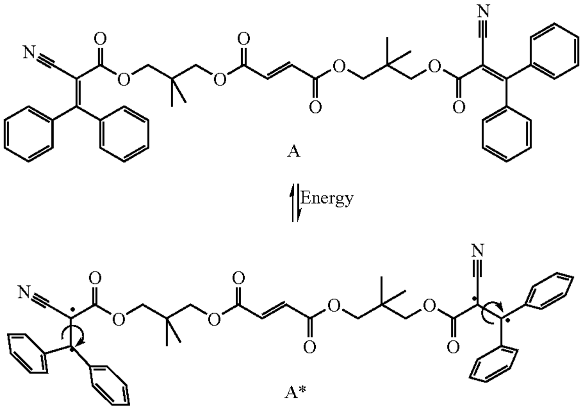

A
A* wherein Di(NPG Crylene) Fumarate, shown above as A, is shown to accept the triplet excited state energy and each crylene moiety forms a diradical (shown above as A*) at the α and β positions of the acrylate, which converts the double bond into a single bond and allows for free rotation about the single bond. This rotation occurs rapidly and efficiently to dissipate excited state energy accepted by a diester that includes one or more crylene moieties.

It has also surprisingly been found that the addition of one or more of a diester that includes one or more fluorene moieties (e.g., Di(NPG Fluorene) Maleate) increases the photostability of a sunscreen composition. Without intending to be limited to any particular mechanism by which a such compounds are able to quench (accept the excited state energy) an excited photoactive compound, it is believed that diesters containing one or more of a fluorene moiety accept the excited state energy and dissipates the energy kinetically in the form of rapid isomerizations. An example of this process is shown below:

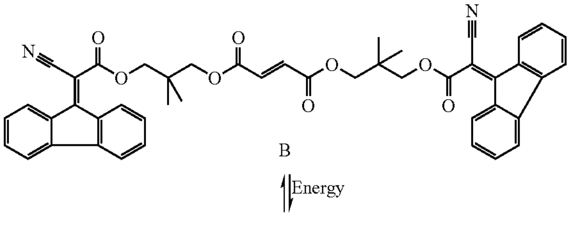

B

-continued

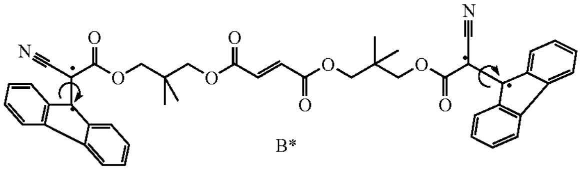

B* wherein Di(NPG Fluorene) Fumarate, shown above as B, is shown to accept the triplet excited state energy and each crylene moiety forms a diradical (shown above as B*) at the α and β positions of the acrylate, which converts the double bond into a single bond and allows for free rotation about the single bond. This rotation occurs rapidly and efficiently to dissipate excited state energy accepted by a diester that includes one or more fluorene moieties. In solution (e.g., a sunscreen composition), a key limitation on the ability of a compound to photostabilize another compound is the ability of the two compounds to come into contact with one another. See Bonda at al., U.S. patent application Ser. Nos. 10/246,434, 10/302,423, and 10/385,833, the disclosures of which are hereby incorporated by reference.

Commonly-assigned U.S. Pat. Nos. 6,485,713 and 6,537,529, the disclosures of which are hereby incorporated herein by reference, describe compositions and methods for increasing the stability of photoactive compounds in a sunscreen composition, e.g., by the addition of polar solvents to the oil phase of a composition. It has been found, quite surprisingly, that by increasing the polarity of the oil phase of a sunscreen composition including one or more of a diester that includes two crylene moieties (e.g., Di(NPG Crylene) Maleate), a diester that includes two fluorene moieties (e.g., Di(NPG Fluorene) Maleate), and/or a diester that includes one crylene moiety and one fluorene moiety, the stability of the sunscreen composition is increased. Now knowing that the polarity of the solution affects the stability, one might expect that the more polar the solution is, the greater the stability it will impart to the photoactive compound. In contrast, and even more surprisingly, it has been found that as the polarity of a solvent system including a dissolved, rapidly photodegradable compound is increased, the rate of photodecay initially decreases but then increases again as the polarity is further increased. Thus, a photodegradable compound in solution will degrade as a second-order function of the overall polarity of the solution. Currently accepted photochemical theory provides the possibility that the mechanism by which a photodegradable compound is stabilized is the transfer of a photonically-excited electron to a nearby molecule of the same or different species (see, e.g., N. J. Turro, Modern Molecular Photochemistry, Chapter 9, Benjamin/Cummings Publ. Co., Menlo Park, Calif. (1991)), however photochemical theory does not describe the observed phenomena. Though not intending to be bound by such a belief, the observed phenomena are believed to coincide with the electron transfer theory of Professor Rudolph A. Marcus of the California Institute of Technology, for which he received the 1992 Nobel Prize in Chemistry.

The dielectric constant of a solvent system is a preferred measure of polarity of a solvent system, for example because the dielectric constant is a measure of both inherent and inducible dipole moments. Other measures of polarity include, but are not limited to, the induced and/or inherent (permanent) dipole moment (e.g., in Debye units), the Dimroth-Reichardt ET parameter, and ionizing power. See generally, C. Reichardt, "Solvents and Solvent Effects in Organic Chemistry" 2nd ed., Chap. 7: Empirical Parameters of Solvent Polarity, VCH Publishers, New York, N.Y., (1988). Moreover, a more detailed description of these methods of measuring the polarity of the compound or a series of compounds can be found in commonly assigned U.S. Pat. Nos. 6,485,713 and 6,537,529.

Mathematically, photodegradation can be described by an exponential function. Thus, Q(a), the absorbance after a radiation dose (i.e., exposure to a quantity of radiation), can be described by the general equation (i), $$Q(a)=Ae^{-kr} \quad \text{(i)}$$

wherein A is the original (pre-exposure) absorbance, e is the natural logarithm base, k is the rate constant of the photodecay, and r is the cumulative dose (e.g., in MED units). Because the absorbance decreases as the cumulative dose increases (photodecay), the overall term −k will be negative, and the greater the value of −k (i.e., closer to zero) and, thus, the lower the rate constant of photodecay, the lower is the rate of photodecay. For example, when Q(a) is plotted on a log scale versus r on a linear scale, the function forms a straight line with a slope equal to −k.

Furthermore, it has been found that, for a set of photoactive compounds that includes a photodegradable compound (e.g. avobenzone), the rate constant of photodecay of the set of photoactive compounds can be described as a second-order function of the polarity, preferably the dielectric constant (i.e., relative permittivity) of the filter set dissolved in the solvent system. Thus, for example, the rate constant of photodecay of a filter set that include one or more of a photoactive compound, can be described by the general equation (ii), $$k=-(x\epsilon^2+y\epsilon+z) \quad \text{(ii)}$$

wherein x, y, and z can be empirically determined. The dielectric constant at the theoretical minimum rate constant of photodecay −k min described by formula (iii), $$\varepsilon_{k\,\min} = \frac{-y}{2x} \quad \text{(iii)}$$

wherein x and y are defined as above.

The phenomena described above, coupled with the knowledge that, heretofore, sunscreen compositions have been formulated without specific regard to the relationship between polarity and photostability and, in newly-discovered fact, have had non-optimal polarities, forms the basis for at least one aspect of the compositions and methods described herein.

In a sunscreen disclosed herein, preferably, one or more of a highly polar solvent is present in the oil-phase of the composition. Preferably, a sufficient amount of a polar solvent is present in a sunscreen composition to raise the dielectric constant of the oil-phase of the composition to a dielectric constant of at least about 7, preferably at least about 8.

A photoactive compound is one that responds to light photoelectrically. In the compositions disclosed herein, a photoactive compound is one that responds to UV radiation photoelectrically. For example, photoactive compounds that respond to UV radiation photoelectrically by rapid photodegradation can benefit highly from the compositions and methods disclosed herein, even though the benefits of the compositions and methods disclosed herein are not limited to such compounds. Photostability is a potential problem with all UV filters because they are deliberately selected as UV-absorbing molecules. In other applications, a photoactive compound may be a pigment or a dye (e.g., a hydrophobic dye).

UV filters include compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl-5-sulfoniobenzoxazoic acid, and combinations thereof.

For a product marketed in the United States, preferred cosmetically-acceptable photoactive compounds and concentrations (reported as a percentage by weight of the total cosmetic sunscreen composition) include: aminobenzoic acid (also called para-aminobenzoic acid and PABA; 15% or less), avobenzone (also called butyl methoxy dibenzoylmethane; 3% or less), cinoxate (also called 2-ethoxyethyl p-methoxycinnamate; 3% or less), dioxybenzone (also called benzophenone-8; 3% or less), homosalate (15% or less), menthyl anthranilate (also called menthyl 2-aminobenzoate; 5% or less), octocrylene (also called 2-ethylhexyl-2-cyano-3,3 diphenylacrylate; 10% or less), octyl methoxycinnamate (7.5% or less), octyl salicylate (also called 2-ethylhexyl salicylate; 5% or less), oxybenzone (also called benzophenone-3; 6% or less), padimate O (also called octyl dimethyl PABA; 8% or less), phenylbenzimidazole sulfonic acid (water soluble; 4% or less), sulisobenzone (also called benzophenone-4; 10% or less), titanium dioxide (25% or less), trolamine salicylate (also called triethanolamine salicylate; 12% or less), and zinc oxide (25% or less).

Other preferred cosmetically-acceptable photoactive compounds and preferred concentrations (percent by weight of the total cosmetic sunscreen composition) include diethanolamine methoxycinnamate (10% or less), ethyl-[bis(hydroxypropyl)] aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less).

For a product marketed in the European Union, preferred cosmetically-acceptable photoactive compounds and preferred concentrations (reported as a percentage by weight of the total cosmetic sunscreen composition) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bis-ethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine. (10% or less, also called TINOSORB S).

All of the above-described UV filters are commercially available. For example, suitable commercially-available organic UV filters are identified by trade name and supplier in Table I below:

TABLE I

| CTFA Name | Trade Name | Supplier |
|---|---|---|
| benzophenone-3 | UVINULM-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| ethyl dihydroxypropyl-PABA | AMERSCREEN P | Amerchol Corp. |
| glyceryl PABA | NIPA G.M.P.A. Continued | Nipa Labs. |
| homosalate | KEMESTER HMS | Humko Chemical |
| menthyl anthranilate | SUNAROME UV-A | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)- | EUSOLEX 6300 | EM Industries |

TABLE I-continued

| CTFA Name | Trade Name | Supplier |
|---|---|---|
| camphor | | |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 Continued | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine. | TINOSORB S | Ciba Specialty Chemicals |

The term "alkyl" as used herein refers to straight- and branched-chain hydrocarbon groups, preferably containing one to thirty carbon atoms. Examples of alkyl groups are $C_1$-$C_4$ alkyl groups. As used herein the designation $C_x$-$C_y$, wherein x and y are integers, denotes a group having from x to y carbon atoms, e.g., a $C_1$-$C_4$ alkyl group is an alkyl group having one to four carbon atoms. Nonlimiting examples of alkyl groups include, methyl, ethyl, n-propyl, isopropyl, n-butyl, sec-butyl (2-methylpropyl), t-butyl (1,1-dimethylethyl), and 3,3-dimethylpentane.

The term "cycloalkyl" as used herein refers to an aliphatic cyclic hydrocarbon group, preferably containing three to eight carbon atoms. Nonlimiting examples of cycloalkyl groups include cyclopropyl, cyclobutyl, cyclopentyl, and cyclohexyl.

The term "alkylene" as used herein includes both straight chained, branched, and cyclic hydrocarbon radicals that include at least one carbon-carbon double bond, preferably, an alkylene group contains between two and thirty carbon atoms. Nonlimiting examples alkylene groups include methylene, ethylene, propylene, butylene, and isopropylene.

The term "alkyne" as used herein includes both straight and branched chained hydrocarbon radicals having at least one carbon-carbon triple bond, preferably, an alkyne group contains between two and thirty carbon atoms.

The terms "substituted alkyl," "substituted cycloalkyl," "substituted alkylene," and "substituted alkyne" as used herein refer to an alkyl, cycloalkyl, alkylene, or alkyne group having one or more substituents. Substituents can include, but are not limited to, alkyl, cycloalkyl, alkylene, alkyne, heteroaryl, heterocycloalkyl, aryl, substituted aryl, substituted heteroaryl, substituted heterocycloalkyl, hydroxyl, ester, carboxy, cyano, amino, amido, sulfur, and halo. Preferred substituted alkyl groups have one to twenty carbon atoms, not including carbon atoms of the substituent group. Preferably, a substituted alkyl group is mono- or di-substituted at one, two, or three carbon atoms. The substituents can be bound to the same carbon or different carbon atoms.

The term "ester" as used herein refers to a group of the general formula:

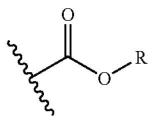

wherein R is an alkyl group, alkylene group, alkyne group, cycloalkyl group, substituted alkyl group, substituted alkylene group, substituted alkyne group, or a substituted cycloalkyl group.

The term "aryl" as used herein refers to monocyclic, fused bicyclic, and fused tricyclic carbocyclic aromatic ring systems including, but not limited to, phenyl, naphthyl, tetrahydronaphthyl, phenanthrenyl, biphenylenyl, indanyl, indenyl, anthracenyl, and fluorenyl.

The term "heteroaryl" as used herein refers to monocyclic, fused bicyclic, and fused tricyclic aromatic ring systems, wherein one to four-ring atoms are selected from the group consisting of oxygen, nitrogen, and sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, thiophenyl, furanyl, quinolinyl, isoquinolinyl, benzoxazolyl, benzimidazolyl, and benzothiazolyl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "substituted aryl," "substituted heteroaryl," and "substituted heterocycloalkyl" as used herein refer to an aryl, heteroaryl, or heterocycloalkyl group substituted by a replacement of one, two, or three of the hydrogen atoms thereon with a substitute selected from the group consisting of alkyl, alkylene, alkyne, substituted alkyl, substituted cycloalkyl, substituted alkylene, substituted alkyne, ether, amino, aryl, heteroaryl, cycloalkyl, heterocycloalkyl, $O(CH_2)_{1-3}N(R)_2$, $O(CH_2)_{1-3}CO_2H$, hydroxyl, ester, carboxy, cyano, amino, amido, sulfur, and halo.

The term "amino" as used herein refers an $—NH_2$ or —NH— group, wherein each hydrogen in each formula can be replaced with an alkyl, cycloalkyl, aryl, heteroaryl, heterocycloalkyl, substituted alkyl, substituted cycloalkyl, substituted aryl, substituted heteroaryl, or substituted heterocycloalkyl group, i.e., $N(R)_2$. In the case of $—NH_2$, the hydrogen atoms also can be replaced with substituents taken together to form a 5- or 6-membered aromatic or non-aromatic ring, wherein one or two carbons of the ring optionally are replaced with a heteroatom selected from the group consisting of sulfur, oxygen, and nitrogen. The ring also optionally can be substituted with an alkyl group. Examples of rings formed by substituents taken together with the nitrogen atom include morpholinyl, phenylpiperazinyl, imidazolyl, pyrrolidinyl, (N-methyl)piperazinyl, and piperidinyl.

The term “amido” as used herein refers to a moiety of the general formula:

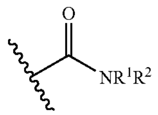

wherein $R^1$ and $R^2$ are the same or different and selected from hydrogen, alkyl, alkylene, alkyne, substituted alkyl, substituted alkylene, substituted alkyne, aryl, alkylene aryl, heteroaryl, and alkylene heteroaryl.

The term “cyano” as used herein refers to a —C≡N group, also designated—CN.

The term “halo” as used herein refers to fluorine, chlorine, bromine, and iodine.

The term “carboxy” as used herein refers to a moiety of the general formula:

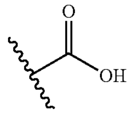

The term “sulfur” as used herein refers to a neutral sulfur atom that is unsubstituted or substituted with one or more of a neutral species, including any oxidized or reduced form of sulfur (e.g., $—SO_2—$). Nonlimiting examples of sulfur groups include sulfites, sulfides, sulfates, and alkyl sulfides.

The term “hydroxyl” as used herein refers to an —OH group.

A sunscreen composition disclosed herein can include a variety of photoactive compounds, including one or more UV-A photoactive compounds and one or more UV-B photoactive compounds. Preferably, a sunscreen composition includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof, trihydroxycinnamic acid and derivatives thereof, dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives; methoxy-substituted benzophenone derivatives; uric acid derivatives; vilouric acid derivatives; tannic acid and derivatives thereof; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations of the foregoing.

UV-A radiation (about 320 nm to about 400 nm), is recognized as contributing to causing damage, to skin particularly to very lightly-colored or sensitive skin. A sunscreen composition disclosed herein preferably includes a UV-A photoactive compound. Preferably, a sunscreen composition disclosed herein includes a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

A preferred combination of photoactive compounds in a sunscreen composition includes a UV-A and a UV-B photoactive compound. However, when 2-ethylhexyl-p-methoxycinnamate is included in a mixture with a dibenzoylmethane derivative, the dibenzoylmethane derivative can become particularly unstable. Without intending to be limited to any particular mechanism, it is believed that the cinnamate ester reacts with an excited-state dibenzoylmethane derivative in a bimolecular pathway that renders both the dibenzoylmethane derivative and the cinnamate ester incapable of absorbing UV radiation. It has been found, quite surprisingly, that the use of one or more of a diester that includes two crylene moieties (e.g., Di(NPG Crylene) Maleate), a diester that includes two fluorene moieties (e.g., Di(NPG Fluorene) Maleate), and/or a diester that includes one crylene moiety and one fluorene moiety increases the stability of a sunscreen composition that includes 2-ethylhexyl-p-methoxycinnamate and a dibenzoylmethane derivative. Thus, one embodiment of a sunscreen composition includes 2-ethylhexyl-p-methoxycinnamate, a dibenzoylmethane derivative, and one or more of a diester that includes two crylene moieties (e.g., Di(NPG Crylene) Maleate), a diester that includes two fluorene moieties (e.g., Di(NPG Fluorene) Maleate), and/or a diester that includes one crylene moiety and one fluorene moiety.

Crylene and fluorene diesters described herein can be prepared by a two step process. First, the crylene/fluorene moiety is derivatized with a spacer unit that includes a moiety for attachment (e.g., a alkyl diol), and second, the derivatized crylene moiety is then used to esterify a dibasic acid (e.g., maleic or fumaric acid.)

One embodiment of the compounds, compositions, and methods disclosed herein includes a compound of formula (I):

(I)

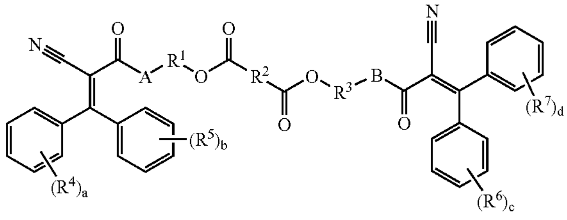

wherein A and B are the same or different and are selected from the group consisting of oxygen, amino and sulfur; $R^1$ and $R^3$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$ is selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^4$, $R^5$, $R^6$ and $R^7$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and a, b, c and d are each in the range of 0 to 4.

Another embodiment of the compounds, compositions, and methods disclosed herein includes a compound of formula (II):

(II)

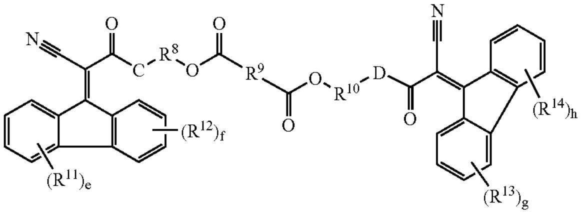

wherein C and D are the same or different and are selected from the group consisting of oxygen, amino and sulfur; $R^8$ and $R^{10}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^9$ is selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^{11}$, $R^{12}$, $R^{13}$ and $R^{14}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl; substituted heteroaryl, substituted heterocycloalkyl, hydroxyl, ester, carboxy, cyano, amino, amido, sulfur and halo; and e, f, g and h are each in the range of 0 to 4.

Another embodiment of the compounds, compositions, and methods disclosed herein includes a compound of formula (III):

(III)

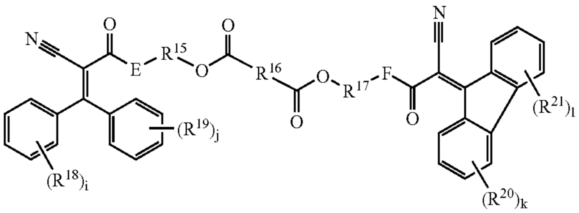

wherein E and F are the same or different and are selected from the group consisting of oxygen, amino and sulfur; $R^{15}$ and $R^{17}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{16}$ is selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^{18}$, $R^{19}$, $R^{20}$ and $R^{21}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and i, j, k and l are each in the range of 0 to 4.

In each of the compounds of formulae (I), (II), and (III) disclosed herein, the R group in the center of the compounds of formulae (I), (II), and (III) ($R^2$, $R^9$ and $R^{16}$) are preferably selected from the groups that can provide a certain amount of rigidity to the compound to provide enough space between the two crylene/fluorene moieties to avoid an undesirable steric interaction between the two crylene/fluorene moieties and allow both moieties to efficiently dissipate energy through rapid isomerizations as described above. Thus, preferably the groups $R^2$, $R^9$ and $R^{16}$ in the compounds of formulae (I), (II), and (III) are selected from the group consisting of $C_2$-$C_{30}$ alkylene, $C_2$-$C_{30}$ alkyne, $C_2$-$C_{30}$ substituted alkylene, and $C_2$-$C_{30}$ substituted alkyne, more preferably selected from the group consisting of $C_2$-$C_{10}$ alkylene, and still more preferably selected from the group consisting of (2E)but-2-ene and (2Z)but-2-ene. In each of the compounds of formulae (I), (II), and (III) disclosed herein, the R groups that are not resident on the aromatic rings and not in the center of the compounds of formulae (I), (II), and (III) ($R^1$, $R^3$, $R^8$, $R^{10}$, $R^{15}$ and $R^{17}$) are preferably selected from $C_2$-$C_{15}$ branched chain alkyls, more preferably 3,3-dimethyl propane. Also preferred in the compounds of formulae (I), (II), and (III) disclosed herein, the groups A, B, C, D, E, and F are oxygen.

Compounds of formula (I), compounds of formula (II), and compounds of formula (III), quite surprisingly, are able to stabilize one or more photoactive compounds present in a sunscreen composition. Preferably, a composition including one or more of a compound of formula (I), a compound of formula (II), and/or a compound of formula (III) also includes a dibenzoylmethane derivative. Without intending to be limited to any particular mechanism of stabilization, it is believed that the photoactive compounds are stabilized by transferring their excited state energy (e.g., singlet and triplet energy) to a diester derivative containing crylene and/or fluorene moieties. It is believed that the transfer of excited state energy takes place because it leads to the most efficient dissipation of the excited state energy (e.g., through the rapid isomerizations discussed above).

Compounds of formula (I), compounds of formula (II), and compounds of formula (III), quite surprisingly, are able to increase the stability of a photoactive compound in a sunscreen composition. Accordingly, another embodiment of the compounds, compositions, and methods disclosed herein is a sunscreen composition, including a mixture of a photoactive compound and a compound selected from the group consisting of compounds of formula (I), compounds of formula (II), compounds of formula (III), and combinations thereof:

(I)

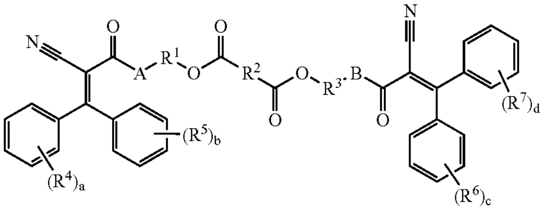

(II)

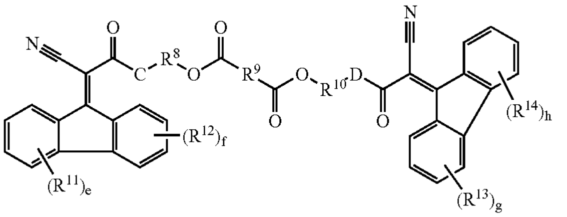

(III)

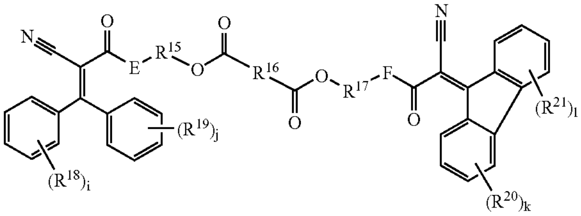

wherein A, B, C, D, E and F are the same or different and are selected from the group consisting of oxygen, amino and sulfur; $R^1$, $R^3$, $R^8$, $R^{10}$, $R^{15}$ and $R^{17}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$, $R^9$ and $R^{16}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^4$, $R^5$, $R^6$, $R^7$, $R^{11}$, $R^{12}$, $R^{13}$, $R^{14}$, $R^{18}$, $R^{19}$, $R^{20}$ and $R^{21}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and a, b, c, d, e, f, g, h, i, j, k and l are each in the range of 0 to 4.

It is preferred that a compound selected from the group consisting of compounds of formula (I), compounds of formula (II), and compounds of formula (III) is present in a sunscreen composition disclosed herein in a range of about 0.1% to about 25% by weight of the total weight of the composition, more preferably about 0.1% to about 10%, still more preferably about 0.5% to about 5%. In a sunscreen composition disclosed herein wherein compounds of formula (I), compounds of formula (II), and compounds of formula (III) are used in combination in the composition, such combination of compounds is preferably present in the composition in a range of about 0.1% to about 50% by weight of the total weight of the composition, more preferably about 0.1% to about 25%, still more preferably about 0.5% to about 10%.

Compounds of formula (I), compounds of formula (II), and compounds of formula (III), quite surprisingly, are able to absorb UV-radiation, and are able to act as a photoactive compound to protect other photodegradable UV-absorbing compounds against photodegradation. The compounds of formulae (I), (II), and (III) are therefore able to be used to protect skin from the harmful effects of UV-radiation. FIG. 1 shows the absorbance spectra from 250 nm to 450 nm for Di(NPG Crylene) Maleate at 15 parts-per-million (ppm) in isopropanol. FIG. 1 shows that Di(NPG Crylene) Maleate (a compound of formula (I)) absorbs UV-radiation over a broad range and has a peak absorbance between about 280 nm to about 320 nm. Accordingly, another embodiment of the compounds, compositions, and methods disclosed herein is a method of protecting human skin from ultraviolet radiation including the step of topically applying to the skin, in a cosmetically acceptable carrier, a compound selected from the group consisting of compounds of formula (I), compounds, of formula (II), formula (III), and combinations thereof:

(I)

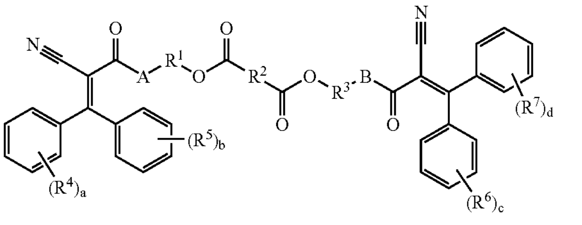

-continued (II)

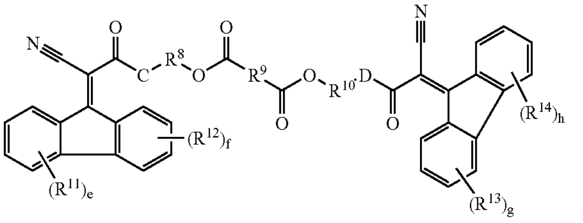

(III)

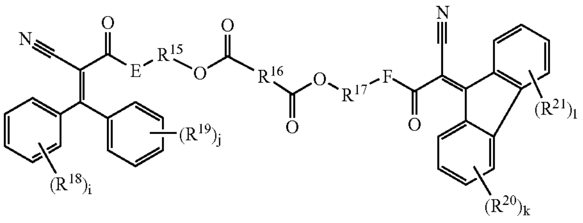

wherein A, B, C, D, E and F are the same or different and are selected from the group consisting of oxygen, amino and sulfur; $R^1$, $R^3$, $R^8$, $R^{10}$, $R^{15}$ and $R^{17}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$, $R^9$ and $R^{16}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^4$, $R^5$, $R^6$, $R^7$, $R^{11}$, $R^{12}$, $R^{13}$, $R^{14}$, $R^{18}$, $R^{19}$, $R^{20}$ and $R^{21}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and a, b, c, d, e, f, g, h, i, j, k and l are each in the range of 0 to 4.

Figure 2:
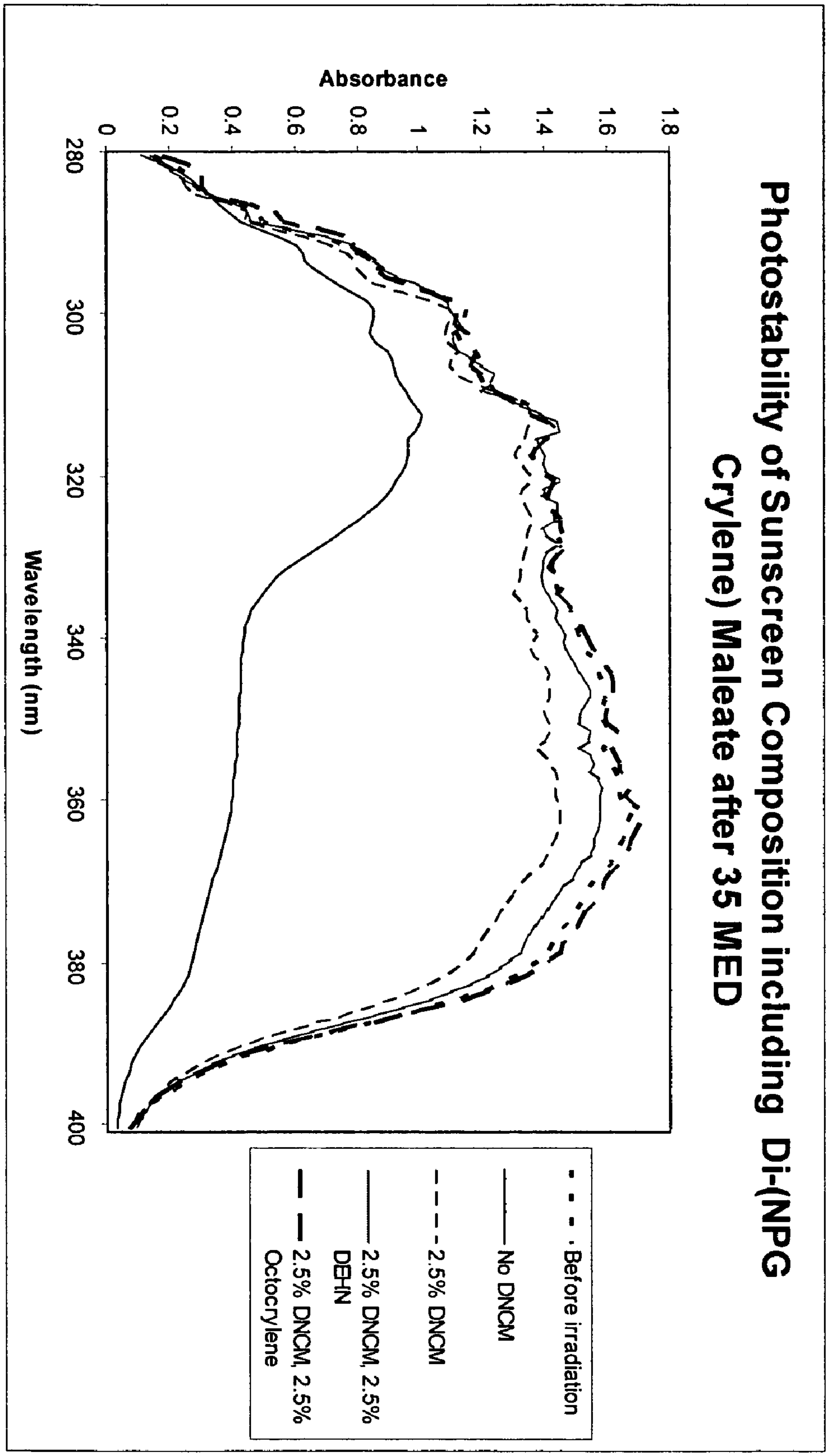
FIG. 2 is a graph of the percent of the original absorbance of a sunscreen composition including 2.5% Di(NPG Crylene) Maleate and 2.5% Octocrylene, a sunscreen composition including 2.5% Di(NPG Crylene) Maleate and 2.5% Diethylhexyl 2,6-naphthalate, a sunscreen composition including only 2.5% Di(NPG Crylene) Maleate, and a sunscreen composition not including 2.5% Di(NPG Crylene) Maleate, wherein the percent absorbance is measured from a wavelength of 280 nm to 400 nm, at a concentration of 10 ppm (parts per million) in cyclohexane, and after the composition has been exposed to 35 MED of radiation.

Compounds of formula (I), compound of formula (II), and compounds of formula (III) are able to increase the stability of a sunscreen composition by both directly absorbing UV-radiation and by increasing the stability of other photoactive compounds in a composition. FIG. 2 is a graph of the absorbance spectra from 280 nm to 400 nm for the sunscreen compositions shown in Table II, wherein a set of composition were prepared to show the ability of Di(NPG Crylene) Maleate (a compound of formula (I)) to stabilize a sunscreen composition and to enhance the stability of other photoactive compounds in the composition. FIG. 2 confirms that Di(NPG Crylene) Maleate absorbs UV-radiation independent of other UV-absorbing agents and increases the stability of the sunscreen composition. Accordingly, another embodiment of the compounds, compositions, and methods disclosed herein is a method of photostabilizing a sunscreen composition including a photoactive compound, the method includes the step of, adding to the sunscreen composition a photostabilizing amount of a compound selected from the group consisting of compounds of formula (I), compounds of formula (II), compounds of formula (III), and combinations thereof:

(I)

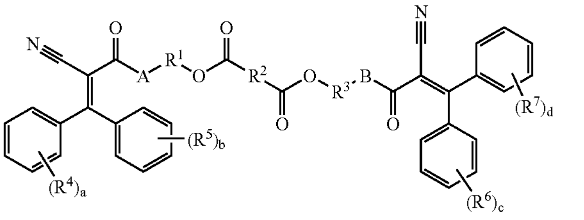

(II)

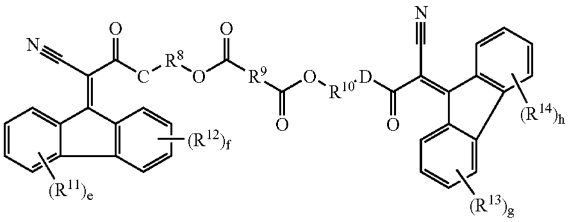

(III)

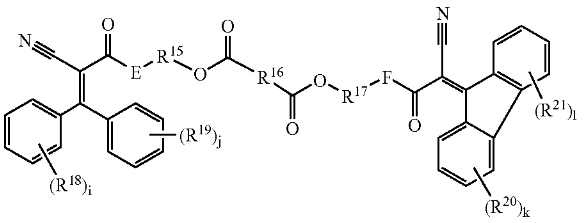

wherein A, B, C, D, E and F are the same or different and are selected from the group consisting of oxygen, amino and sulfur; $R^1$, $R^3$, $R^8$, $R^{10}$, $R^{15}$ and $R^{17}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$, $R^9$ and $R^{16}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^4$, $R^5$, $R^6$, $R^7$, $R^{11}$, $R^{12}$, $R^{13}$, $R^{14}$, $R^{18}$, $R^{19}$, $R^{20}$ and $R^{21}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and a, b, c, d, e, f, g, h, i, j, k and l are each in the range of 0 to 4.

Likewise, compounds of formula (I), compounds of formula (II), and compounds of formula (III), quite surprisingly, are able to increase the photostability of a dibenzoylmethane derivative. Without intending to be limited to a particular mechanism, it is believed that compounds formula (I), compounds of formula (II), and compounds of formula (III) are able to photostabilize a dibenzoylmethane derivative by accepting the triplet excited energy from an excited dibenzoylmethane derivative. Thus, another embodiment of the compounds, compositions, and methods disclosed herein is to provide a method of photostabilizing a dibenzoylmethane derivative, the method includes the step of, adding to the dibenzoylmethane derivative a photostabilizing amount of a compound selected from the group consisting of compounds of formula (I), compounds of formula (II), compounds of formula (III), and combinations thereof:

(I)

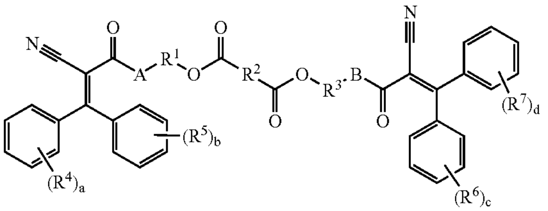

(II)

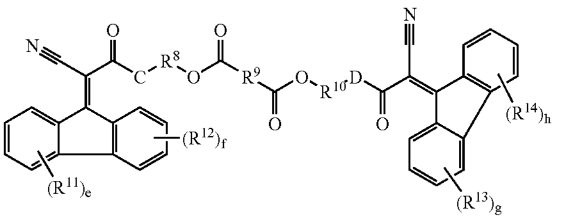

(III)

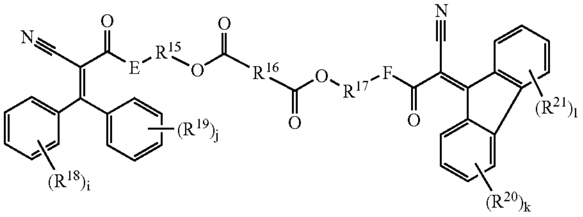

wherein A, B, C, D, E and F are the same or different and are selected from the group consisting of oxygen, amino and sulfur; $R^1$, $R^3$, $R^8$, $R^{10}$, $R^{15}$ and $R^{17}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$, $R^9$ and $R^{16}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^4$, $R^5$, $R^6$, $R^7$, $R^{11}$, $R^{12}$, $R^{13}$, $R^{14}$, $R^{18}$, $R^{19}$, $R^{20}$ and $R^{21}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and a, b, c, d, e, f, g, h, i, j, k and l are each in the range of 0 to 4.

Another embodiment of the compounds, compositions, and methods disclosed herein is a compound of formula (IV):

(IV)

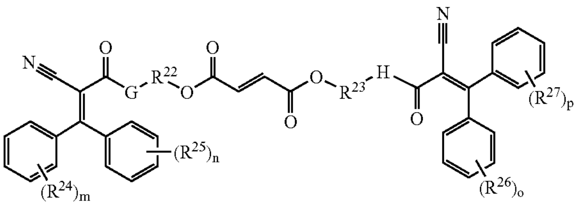

wherein G and H are the same or different and are selected from the group consisting of oxygen, amino and sulfur; $R^{22}$ and $R^{23}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{24}$, $R^{25}$, $R^{26}$ and $R^{27}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and m, n, o and p are each in the range of 0 to 4.

Another embodiment of the compounds, compositions, and methods disclosed herein is a compound of formula (V):

(V)

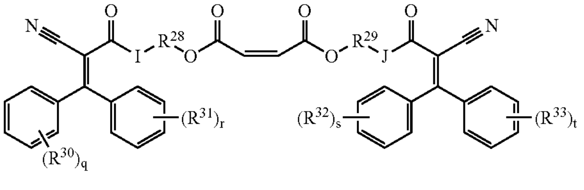

wherein I and J are the same or different and are selected from the group consisting of oxygen, amino and sulfur; $R^{28}$ and $R^{29}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{30}$, $R^{31}$, $R^{32}$ and $R^{33}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and q, r, s and t are each in the range of 0 to 4.

Another embodiment of the compounds, compositions, and methods disclosed herein is a compound of formula (VI):

(VI)

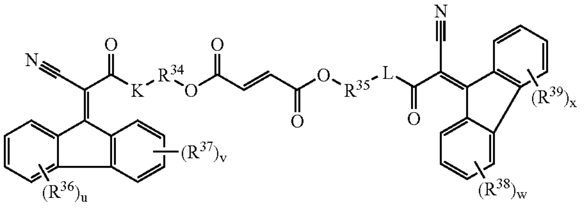

wherein K and L are the same or different and are selected from the group consisting of oxygen, amino and sulfur; $R^{34}$ and $R^{35}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{36}$, $R^{37}$, $R^{38}$ and $R^{39}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and u, v, w and x are each in the range of 0 to 4.

Another embodiment of the compounds, compositions, and methods disclosed herein is a compound of formula (VII):

(VII)

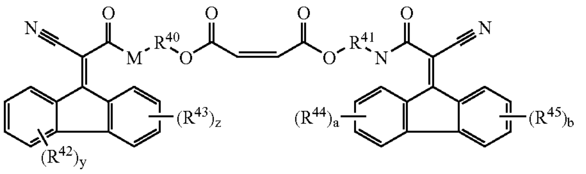

wherein M and N are the same or different and are selected from the group consisting of oxygen, amino and sulfur; $R^{40}$ and $R^{41}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{42}$, $R^{43}$, $R^{44}$ and $R^{45}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and y, z, a and b are each in the range of 0 to 4.

In each of the compounds of formulae (IV), (V), (VI), and (VII) disclosed herein, the R groups that are not resident on the aromatic rings and not in the center of the compound ($R^{22}$, $R^{23}$, $R^{28}$, $R^{29}$, $R^{34}$, $R^{35}$, $R^{40}$ and $R^{41}$) are preferably selected from $C_2$-$C_{15}$ branched chain alkyls, more preferably, 3,3-dimethyl propane. Also preferred in the compounds of formulae (IV), (V), (VI), and (VII) disclosed herein, the groups G, H, I, J, K, L, M and N are oxygen.

Compounds of formula (IV), compounds of formula (V), compounds of formula (VI), and compounds of formula (VII), quite surprisingly, are able to stabilize one or more photoactive compounds present in a sunscreen composition. Preferably, a composition including one or more of a compound of formulae (IV), (V), (VI), and (VII) also includes a dibenzoylmethane derivative. Without intending to be limited to any particular mechanism of stabilization, it is believed that the photoactive compounds are stabilized by transferring their excited state energy (e.g., singlet and triplet energy) to a fumarate or a maleate ester derivative containing two crylene/fluorene moieties. It is believed that the transfer of excited state energy takes place because it leads to the most efficient dissipation of the excited state energy (e.g., through the rapid isomerizations discussed above).

Compounds of formula (IV), compounds of formula (V), compounds of formula (VI), and compounds of formula (VII), quite surprisingly, are able to increase the stability of a photoactive compound in a sunscreen composition. Accordingly, another embodiment of the compounds, compositions, and methods disclosed herein is a sunscreen composition, including a mixture of a photoactive compound and a compound selected from the group consisting of compounds of formula (IV), compounds of formula (V), compounds of formula (VI), compounds of formula (VII), and combinations thereof:

(IV)

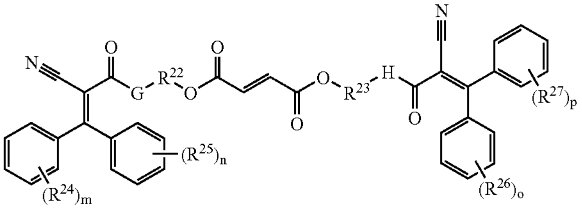

(V)

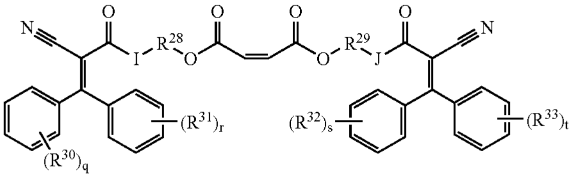

(VI)

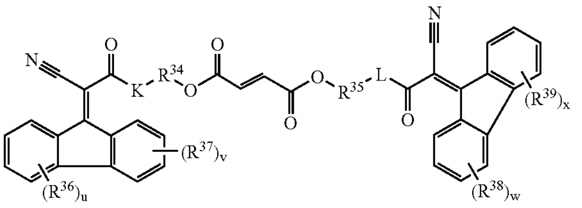

-continued (VII)

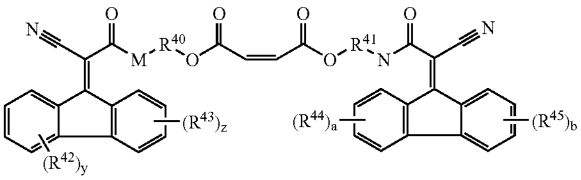

wherein G, H, I, J, K, L, M and N are the same or different and are selected from the group consisting of oxygen, amino and sulfur; $R^{22}$, $R^{23}$, $R^{28}$, $R^{29}$, $R^{34}$, $R^{35}$, $R^{40}$ and $R^{41}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{24}$, $R^{25}$, $R^{26}$, $R^{27}$, $R^{30}$, $R^{31}$, $R^{32}$, $R^{33}$, $R^{36}$, $R^{37}$, $R^{38}$, $R^{39}$, $R^{42}$, $R^{43}$, $R^{44}$ and $R^{45}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and m, n, o, p, q, r, s, t, u, v, w, x, y, z, a and b are each in the range of 0 to 4.

It is preferred that a compound selected from the group consisting of compounds of formula (IV), compounds of formula (V), compounds of formula (VI), and compounds of formula (VII) is present in a sunscreen composition disclosed herein in a range of about 0.1% to about 25% by weight of the total weight of the composition, more preferably about 0.1% to about 10%, still more preferably about 0.5% to about 5%. In a sunscreen composition disclosed herein wherein compounds of formula (IV), compounds of formula (V), compounds of formula (VI), and compounds of formula (VII) are used in combination in the composition, such combination of compounds is preferably present in the composition in a range of about 0.1% to about 50% by weight of the total weight of the composition, more preferably about 0.1% to about 25%, still more preferably about 0.5% to about 10%.

Compounds of formula (IV), compounds of formula (V), compounds of formula (VI), and compounds of formula (VII), quite surprisingly, are able to absorb UV-radiation, and are able to act as a photoactive compound to protect other photodegradable UV-absorbing compounds against photodegradation. The compounds of formulae (IV), (V), (VI), and (VII) are therefore able to be used to protect skin from the harmful effects of UV-radiation. FIG. 1 shows the absorbance spectra from 250 nm to 450 nm for Di(NPG Crylene) Maleate at 15 parts-per-million (ppm) in isopropanol. FIG. 1 shows that Di(NPG Crylene) Maleate (a compound of formula (V)) absorbs UV-radiation over a broad range and has a peak absorbance between about 280 nm to about 320 nm. Accordingly, another embodiment of the compounds, compositions, and methods disclosed herein is a method of protecting human skin from ultraviolet radiation including the step of topically applying to the skin, in a cosmetically acceptable carrier, a compound selected from the group consisting of compounds of formula (IV), compounds of formula (V), compounds of formula (VI), compounds of formula (VII), and combinations thereof:

(IV)

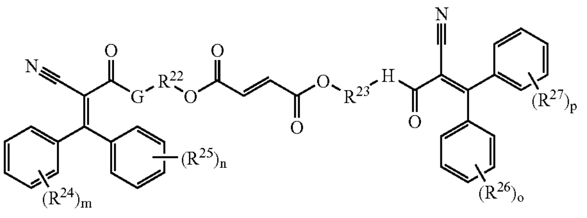

(V)

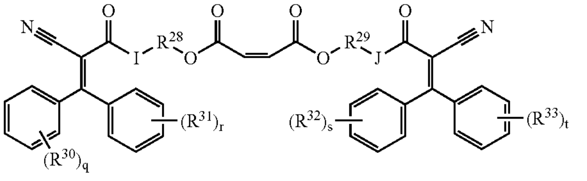

(VI)

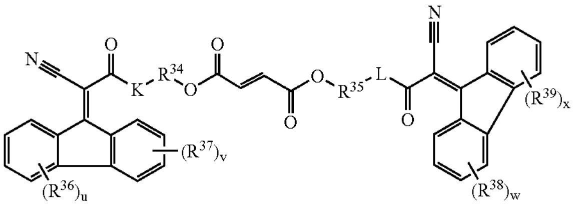

(VII)

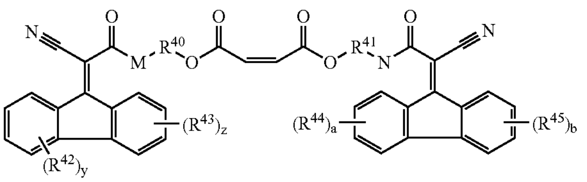

wherein G, H, I, J, K, L, M and N are the same or different and are selected from the group consisting of oxygen, amino and sulfur; $R^{22}$, $R^{23}$, $R^{28}$, $R^{29}$, $R^{34}$, $R^{35}$, $R^{40}$ and $R^{41}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{24}$, $R^{25}$, $R^{26}$, $R^{27}$, $R^{30}$, $R^{31}$, $R^{32}$, $R^{33}$, $R^{36}$, $R^{37}$, $R^{38}$, $R^{39}$, $R^{42}$, $R^{43}$, $R^{44}$ and $R^{45}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and m, n, o, p, q, r, s, t, u, v, w, x, y, z, a and b are each in the range of 0 to 4.

Compounds of formula (IV), compounds of formula (V), compounds of formula (VI), and compounds of formula (VII) are able to increase the stability of a sunscreen composition by both directly absorbing UV-radiation and by increasing the stability of other photoactive compounds in a composition. FIG. 2 is a graph of the absorbance spectra from 280 nm to 400, nm for the sunscreen compositions shown in Table II, wherein a set of composition were prepared to show the ability of Di(NPG Crylene) Maleate (a compound of formula (V)) to stabilize a sunscreen composition and to enhance the stability of other photoactive compounds in the composition. FIG. 2 confirms that Di(NPG Crylene) Maleate absorbs UV-radiation independent of other UV-absorbing agents and increases the stability of the sunscreen composition. Accordingly, another embodiment of the compounds, compositions, and methods disclosed herein is a method of photostabilizing a sunscreen composition including a photoactive compound, the method includes the step of, adding to the sunscreen composition a photostabilizing amount of a compound selected from the group consisting of compounds of formula (IV), compounds of formula (V), compounds of formula (VI), compounds of formula (VII), and combinations thereof:

(IV)

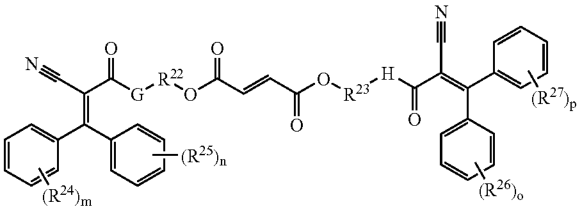

(V)

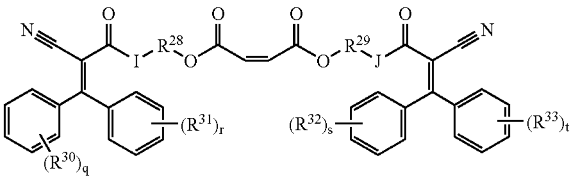

(VI)

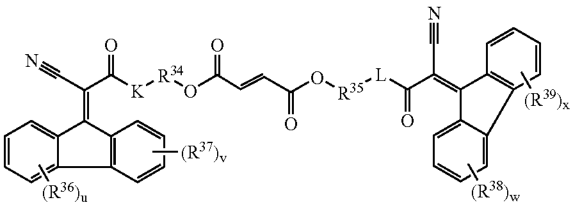

(VII)

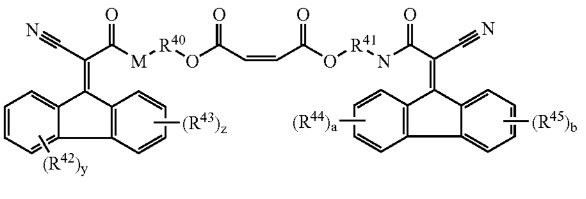

wherein G, H, I, J, K, L, M and N are the same or different and are selected from the group consisting of oxygen, amino and sulfur; $R^{22}$, $R^{23}$, $R^{28}$, $R^{29}$, $R^{34}$, $R^{35}$, $R^{40}$ d $R^{41}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{24}$, $R^{25}$, $R^{26}$, $R^{27}$, $R^{30}$, $R^{31}$, $R^{32}$, $R^{33}$, $R^{36}$, $R^{37}$, $R^{38}$, $R^{39}$, $R^{42}$, $R^{43}$, $R^{44}$ and $R^{45}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and m, n, o, p, q, r, s, t, u, v, w, x, y, z, a and b are each in the range of 0 to 4.

Likewise, compounds of formula (IV), compounds of formula (V), compounds of formula (VI), and compounds of formula (VII), quite surprisingly, are able to increase the photostability of a dibenzoylmethane derivative. Without intending to be limited to a particular mechanism, it is believed that compounds of formula (IV), compounds of formula (V), compounds of formula (VI), and compounds of formula (VII) are able to photostabilize a dibenzoylmethane derivative by accepting the triplet excited energy from an excited dibenzoylmethane derivative. Thus, another embodiment of the compounds, compositions, and methods disclosed herein is to provide a method of photostabilizing a dibenzoylmethane derivative, the method includes the step of, adding to the dibenzoylmethane derivative a photostabilizing amount of a compound selected from the group consisting of compounds of formula (IV), compounds of formula (V), compounds of formula (VI), compounds of formula (VII), and combinations thereof:

(IV)

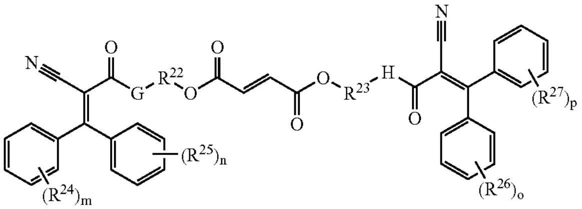

(V)

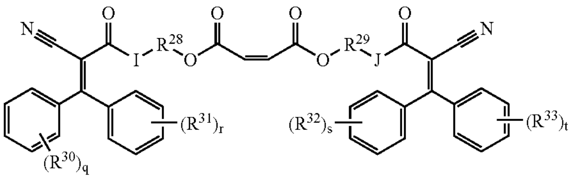

(VI)

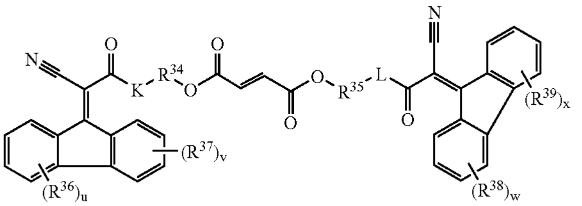

(VII)

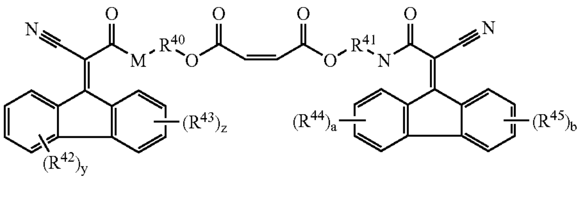

wherein G, H, I, J, K, L, M and N are the same or different and are selected from the group consisting of oxygen, amino and sulfur; $R^{22}$, $R^{23}$, $R^{28}$, $R^{29}$, $R^{34}$, $R^{35}$, $R^{40}$ and $R^{41}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{24}$, $R^{25}$, $R^{26}$, $R^{27}$, $R^{30}$, $R^{31}$, $R^{32}$, $R^{33}$, $R^{36}$, $R^{37}$, $R^{38}$, $R^{39}$, $R^{42}$, $R^{43}$, $R^{44}$ and $R^{45}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and m, n, o, p, q, r, s, t, u, v, w, x, y, z, a and b are each in the range of 0 to 4.

EXAMPLES

The following examples are provided to illustrate the invention but are not intended to limit the scope of the invention.

Example 1

A series of sunscreen compositions was prepared by mixing the ingredients and concentrations (formulations) shown in Table II below:

TABLE II

| Ingredients | 2.5% DNCM and 2.5% Octo-crylene | 2.5% DNCM and 2.5% DEHN | 2.5% DNCM | No DNCM |
|---|---|---|---|---|
| Oil Phase | | | | |
| Avobenzone | 3.00% | 3.00% | 3.00% | 3.00% |
| Octisalate | 5.00% | 5.00% | 5.00% | 5.00% |
| Homosalate | 7.50% | 7.50% | 7.50% | 7.50% |
| Octocrylene | 2.50% | | | |
| Di(NPG Crylene) Maleate (DNCM) | 2.50% | 2.50% | 2.50% | |
| Diethylhexyl 2,6-naphthalate (DEHN) | | 2.50% | | |
| Bodying Agent And Film-Former | | | | |
| Stearyl alcohol | 1.00% | 1.00% | 1.00% | 1.00% |
| $C_{30}$–$C_{38}$ olefin/Isopropyl maleate/MA copolymer | 2.00% | 2.00% | 2.00% | 2.00% |
| Emulsifiers | | | | |
| Steareth 21 | 0.30% | 0.31% | 0.31% | 0.32% |
| Steareth 2 | 0.20% | 0.19% | 0.19% | 0.18% |
| Polyglyceryl-3 methyl glucose distearate | 3.00% | 3.00% | 3.00% | 3.00% |
| Water Phase | | | | |
| Disodium EDTA | 0.05% | 0.05% | 0.05% | 0.05% |
| Glycerin | 3.00% | 3.00% | 3.00% | 3.00% |
| Methylpropanediol | 2.00% | 2.00% | 2.00% | 2.00% |
| Phenoxyethanol & parabens | 0.60% | 0.60% | 0.60% | 0.60% |

TABLE II-continued

| Ingredients | 2.5% DNCM and 2.5% Octo-crylene | 2.5% DNCM and 2.5% DEHN | 2.5% DNCM | No DNCM |
|---|---|---|---|---|
| Stabilizer and Neutralizer | | | | |
| Carbomer | 0.20% | 0.20% | 0.20% | 0.20% |
| Sodium hydroxide (25% solution) | 0.28% | 0.28% | 0.28% | 0.28% |
| Water | 66.87% | 66.87% | 69.37% | 71.87% |

Oil-in-water emulsions were created, wherein the aqueous phase was made up of water, the water phase ingredients, the stabilizer and neutralizer, the emulsifiers, and the bodying agent and film-former listed above. The resulting sunscreens were tested for photostability by measuring absorbance on a Labsphere UV-1000S Ultraviolet Transmittance Analyzer (software version 1.27) before and after irradiation with a Solar Light Company model 16S solar simulator (equipped with a WG 320 filter to transmit radiation greater than 290 nm) in 5 MED increments up to 35 MED. Output was monitored by a PMA 2105 UV-B DCS Detector (biologically weighted) and controlled by a PMA 2100 Automatic Dose Controller (Solar Light Co.).

To test stability, a slide was positioned on the UV transmittance analyzer using registration marks, and a scan of a 1 cm spot on the slide was performed. The slide was then transferred to a holder placed adjacent to the solar simulator and, using a calipers, was positioned such that the beam of UV radiation exiting the solar simulator illuminated the same 1 cm spot on the slide. The following software settings were used: UV-B=290-320 nm; UV-A=320-400 nm. Following an exposure of 5 MED, the slide was again placed in position on the UV transmittance analyzer, and a scan of the exposed spot was performed. The procedure was repeated on the same 1 cm spot on the slide until the desired total radiation dosage was achieved.

FIG. 2 is a graph of the percent absorbance of the sunscreen compositions listed in Table II after exposure to 35 MED of radiation. As shown in FIG. 2, a composition including 2.5% Di(NPG Crylene) Maleate is made more photostable by the addition of the Di(NPG Crylene) Maleate. Moreover, a composition that includes 2.5% Di(NPG Crylene) Maleate and 2.5% Octocrylene is especially photostable and exhibits very little loss in photostability after exposure to 35 MED of radiation.

What is claimed is:

1. A compound of formula (I):

(I)

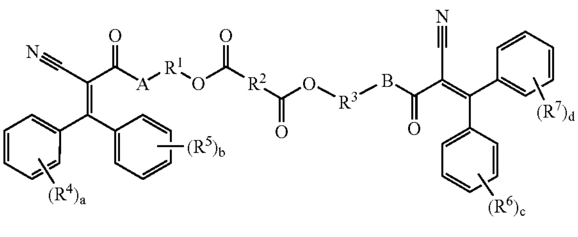

wherein A and B are the same or different and are selected from the group consisting of oxygen, amino and sulfur; $R^1$ and $R^3$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$ is selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^4$, $R^5$, $R^6$ and $R^7$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and a, b, c and d are each in the range of 0 to 4.

2. The compound of claim 1, wherein $R^1$ and $R^3$ are selected from the group consisting of $C_2$-$C_{15}$ alkyl.

3. The compound of claim 2, wherein $R^1$ and $R^3$ are the same and are 3,3-dimethyl propane.

4. The compound of claim 1, wherein $R^2$ is selected from the group consisting of $C_2$-$C_{10}$ alkylene.

5. The compound of claim 4, wherein $R^2$ is selected from the group consisting of (2E)but-2-ene and (2Z)but-2-ene.

6. The compound of claim 1, wherein A and B are oxygen.

7. A compound of formula (II):

(II)

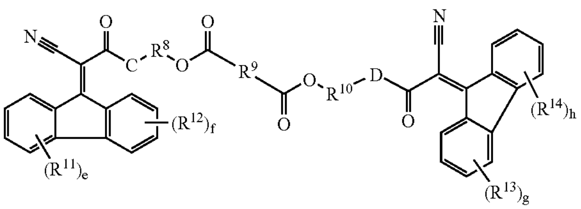

wherein C and D are the same or different and are selected from the group consisting of oxygen, amino and sulfur; $R^8$ and $R^{10}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^9$ is selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^{11}$, $R^{12}$, $R^{13}$ and $R^{14}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and e, f, g and h are each in the range of 0 to 4.

8. The compound of claim 7, wherein $R^8$ and $R^{10}$ are selected from the group consisting of $C_2$-$C_{15}$ alkyl.

9. The compound of claim 8, wherein $R^8$ and $R^{10}$ are the same and are 3,3-dimethyl propane.

10. The compound of claim 7, wherein $R^9$ is selected from the group consisting of $C_2$-$C_{10}$ alkylene.

11. The compound of claim 10, wherein $R^9$ is selected from the group consisting of (2E)but-2-ene and (2Z)but-2-ene.

12. The compound of claim 7, wherein C and D are oxygen.

13. A compound of formula (III):

(III)

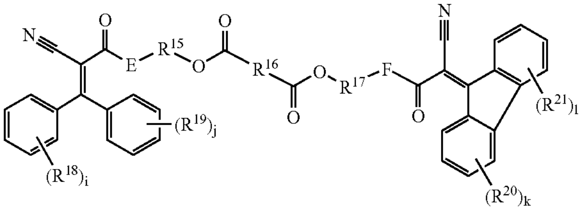

wherein E and F are the same or different and are selected from the group consisting of oxygen, amino and sulfur; $R^{15}$ and $R^{17}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{16}$ is selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^{18}$, $R^{19}$, $R^{20}$ and $R^{21}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and i, j, k and l are each in the range of 0 to 4.

14. The compound of claim 13, wherein $R^8$ and $R^{10}$ are selected from the group consisting of $C_2$-$C_{15}$ alkyl.

15. The compound of claim 14, wherein $R^8$ and $R^{10}$ are the same and are 3,3-dimethyl propane.

16. The compound of claim 13, wherein $R^9$ is selected from the group consisting of $C_2$-$C_{10}$ alkylene.

17. The compound of claim 16, wherein $R^9$ is selected from the group consisting of (2E)but-2-ene and (2Z)but-2-ene.

18. The compound of claim 13, wherein E and F are oxygen.

19. A sunscreen composition, comprising a mixture of a photoactive compound and a compound selected from the group consisting of compounds of formula (I), compounds of formula (II), compounds of formula (III), and combinations thereof:

(I)

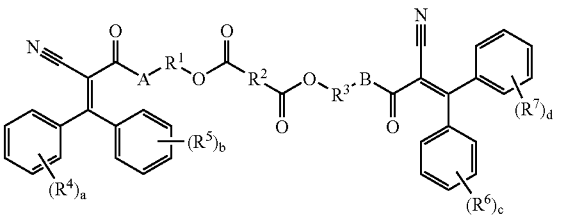

(II)

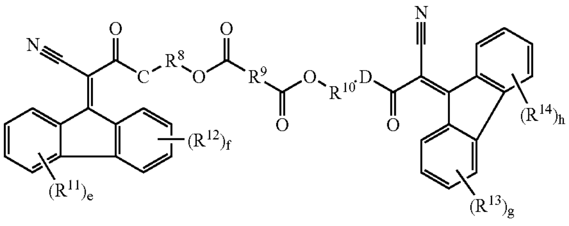

(III)

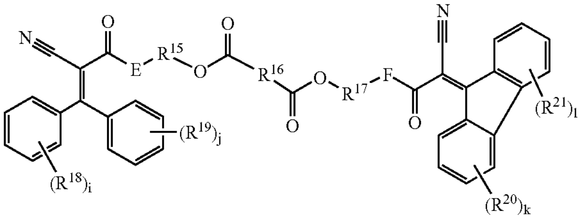

wherein A, B, C, D, E and F are the same or different and are selected from the group consisting of oxygen, amino and sulfur; $R^1$, $R^3$, $R^8$, $R^{10}$, $R^{15}$ and $R^{17}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$, $R^9$ and $R^{16}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^4$, $R^5$, $R^6$, $R^7$, $R^{11}$, $R^{12}$, $R^{13}$, $R^{14}$, $R^{18}$, $R^{19}$, $R^{20}$ and $R^{21}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and a, b, c, d, e, f, g, h, i, j, k and l are each in the range of 0 to 4.

20. The composition of claim 19, wherein $R^1$, $R^3$, $R^8$, $R^{10}$, $R^{15}$ and $R^{17}$ are selected from the group consisting of $C_2$-$C_{15}$ alkyl.

21. The composition of claim 20, wherein $R^1$ and $R^3$ are each 3,3-dimethylpropane.

22. The composition of claim 20, wherein $R^8$ and $R^{10}$ are each 3,3-dimethylpropane.

23. The composition of claim 20, wherein $R^{15}$ and $R^{17}$ are each 3,3-dimethylpropane.

24. The composition of claim 19, wherein A, B, C, D, E and F are each oxygen.

25. The composition of claim 19, further comprising a diester or polyester of naphthalene dicarboxylic acid selected from the group consisting of compounds of formulae (XX) and (XXI), and combinations thereof:

(XX)

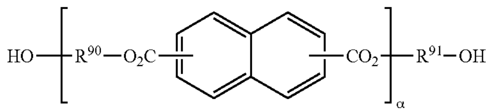

(XXI)

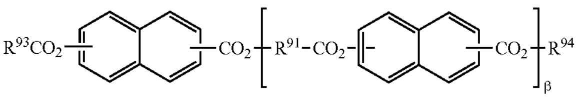

wherein $R^{93}$ and $R^{94}$ are the same or different and selected from the group consisting of $C_1$-$C_{22}$ alkyl groups, diols having the structure HO—$R^{91}$—OH and polyglycols having the structure HO—$R^{90}$—(—O—$R^{91}$—$)_\gamma$—OH; wherein each $R^{90}$ and $R^{91}$ is the same or different and selected from the group consisting of $C_1$-$C_6$ straight or branched chain alkyl groups; and wherein α and γ are each in a range of 1 to 100 and β is in a range of 0 to 100.

26. The composition of claim 19, wherein said compound selected from the group consisting of compounds of formula (I), compounds of formula (II), compounds of formula (III), and combinations thereof is present in a range of about 0.1% to about 50% by weight of the total weight of the composition.

27. The composition of claim 26, wherein said compound selected from the group consisting of compounds of formula (I), compounds of formula (II), compounds of formula (III), and combinations thereof is present in a range of about 0.1% to about 25% by weight of the total weight of the composition.

28. The composition of claim 27, wherein said compound selected from the group consisting of compounds of formula (I), compounds of formula (II), compounds of formula (III), and combinations thereof is present in a range of about 0.1% to about 10% by weight of the total weight of the composition.

29. The composition of claim 19, comprising a dibenzoylmethane derivative.

30. A method of photostabilizing a sunscreen composition comprising a photoactive compound, said method comprising the step of, adding to said sunscreen composition a photostabilizing amount of a compound selected from the group consisting of compounds of formula (I), compounds of formula (II), compounds of formula (III), and combinations thereof:

(I)

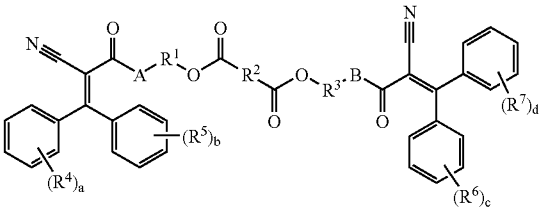

-continued (II)

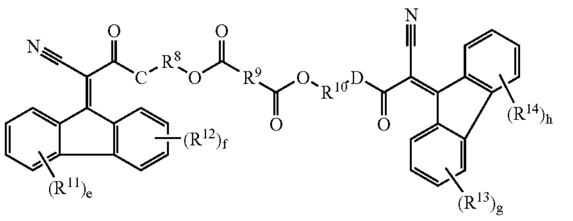

(III)

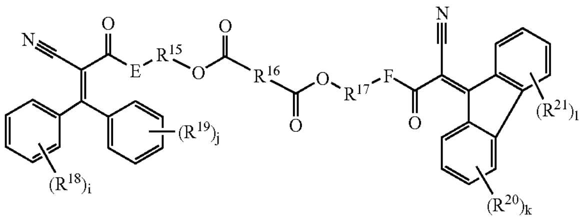

wherein A, B, C, D, E and F are the same or different and are selected from the group consisting of oxygen, amino and sulfur; $R^1$, $R^3$, $R^8$, $R^{10}$, $R^{15}$ and $R^{17}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$, $R^9$ and $R^{16}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^4$, $R^5$, $R^6$, $R^7$, $R^{11}$, $R^{12}$, $R^{13}$, $R^{14}$, $R^{18}$, $R^{19}$, $R^{20}$ and $R^{21}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and a, b, c, d, e, f, g, h, i, j, k and l are each in the range of 0 to 4.

31. The method of claim 30, wherein $R^1$, $R^3$, $R^8$, $R^{10}$, $R^{15}$ and $R^{17}$ are selected from the group consisting of $C_2$-$C_{15}$ alkyl.

32. The method of claim 31, wherein $R^1$ and $R^3$ are each 3,3-dimethylpropane.

33. The method of claim 31, wherein $R^8$ and $R^{10}$ are each 3,3-dimethylpropane.

34. The method of claim 31, wherein $R^{15}$ and $R^{17}$ are each 3,3-dimethylpropane.

35. The method of claim 30, wherein A, B, C, D, E and F are each oxygen.

36. A method of photostabilizing a dibenzoylmethane derivative, said method comprising the step of, adding to said dibenzoylmethane derivative a photostabilizing amount of a compound selected from the group consisting of compounds of formula (I), compounds of formula (II), compounds of formula (III), and combinations thereof:

(I)

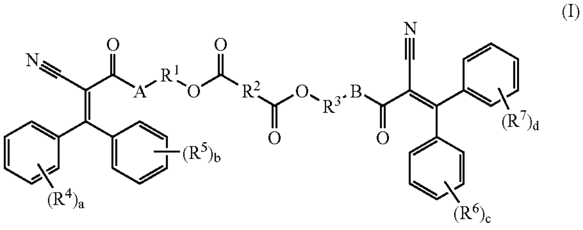

(II)

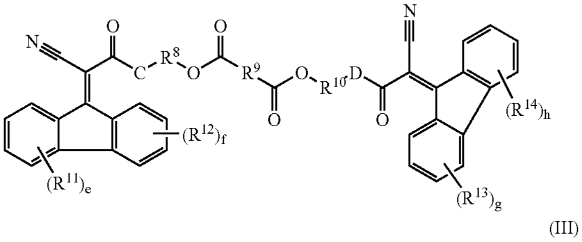

(III)

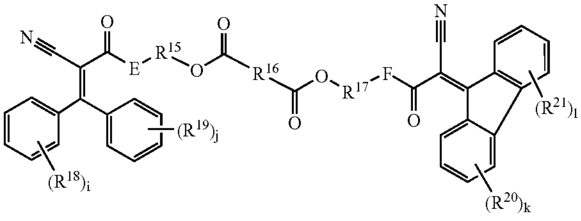

wherein A, B, C, D, E and F are the same or different and are selected from the group consisting of oxygen, amino and sulfur; $R^1$, $R^3$, $R^8$, $R^{10}$, $R^{15}$ and $R^{17}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$, $R^9$ and $R^{16}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R_4$, $R^5$, $R^6$, $R^7$, $R^{11}$, $R^{12}$, $R^{13}$, $R^{14}$, $R^{18}$, $R^{19}$, $R^{20}$ and $R^{21}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and a, b, c, d, e, f, g, h, i, j, k and l are each in the range of 0 to 4.

37. The method of claim 36, wherein $R^1$, $R^3$, $R^8$, $R^{10}$, $R^{15}$ and $R^{17}$ are selected from the group consisting of $C_2$-$C_{15}$ alkyl.

38. The method of claim 37, wherein $R^1$ and $R^3$ are each 3,3-dimethylpropane.

39. The method of claim 37, wherein $R^8$ and $R^{10}$ are each 3,3-dimethylpropane.

40. The method of claim 37, wherein $R^{15}$ and $R^{17}$ are each 3,3-dimethylpropane.

41. The method of claim 36, wherein A, B, C, D, E and F are each oxygen.

42. A method of protecting human skin from ultraviolet radiation comprising topically applying to said skin, in a cosmetically acceptable carrier, a compound selected from the group consisting of compounds of formula (I), compounds of formula (II), compounds of formula (III), and combinations thereof:

(I)

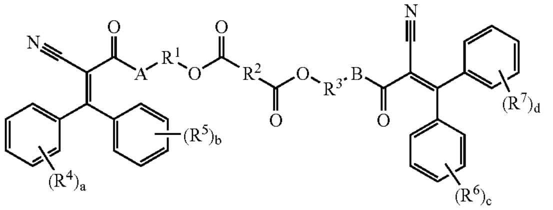

(II)

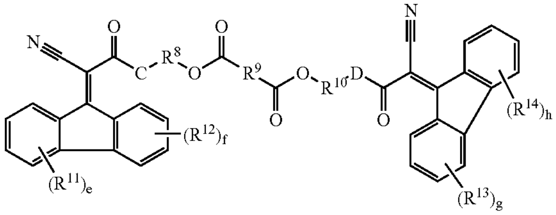

(III)

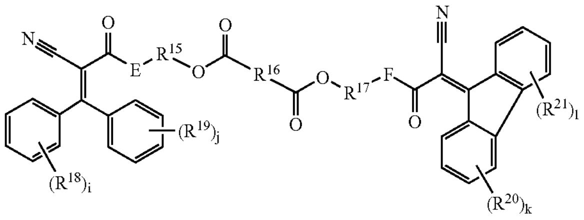

wherein A, B, C, D, E and F are the same or different and are selected from the group consisting of oxygen, amino and sulfur; $R^1$, $R^3$, $R^8$, $R^{10}$, $R^{15}$ and $R^{17}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$, $R^9$ and $R^{16}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne; $R^4$, $R^5$, $R^6$, $R^7$, $R^{11}$, $R^{12}$, $R^{13}$, $R^{14}$, $R^{18}$, $R^{19}$, $R^{20}$ and $R^{21}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and a, b, c, d, e, f, g, h, i, j, k and l are each in the range of 0 to 4.

43. The method of claim 42, wherein $R^1$, $R^3$, $R^8$, $R^{10}$, $R^{15}$ and $R^{17}$ are selected from the group consisting of $C_2$-$C_{15}$ alkyl.

44. The method of claim 43, wherein $R^1$ and $R^3$ are each 3,3-dimethylpropane.

45. The method of claim 43, wherein $R^8$ and $R^{10}$ are each 3,3-dimethylpropane.

46. The method of claim 43, wherein $R^{15}$ and $R^{17}$ are each 3,3-dimethylpropane.

47. The method of claim 42, wherein A, B, C, D, E and F are each oxygen.

48. A compound of formula (IV):

(IV)

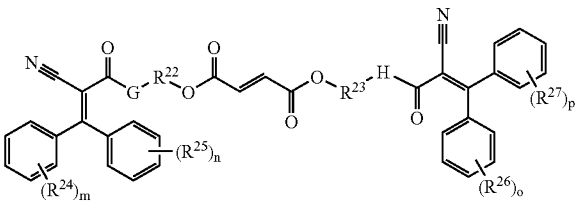

wherein G and H are the same or different and are selected from the group consisting of oxygen, amino and sulfur; $R^{22}$ and $R^{23}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{24}$, $R^{25}$, $R^{26}$ and $R^{27}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and m, n, o and p are each in the range of 0 to 4.

49. The compound of claim 48, wherein $R^{22}$ and $R^{23}$ are selected from the group consisting of $C_2$-$C_{15}$ alkyl.

50. The compound of claim 49, wherein $R^{22}$ and $R^{23}$ are the same and are 3,3-dimethyl propane.

51. The compound of claim 48, wherein G and H are oxygen.

52. A compound of formula (V):

(V)

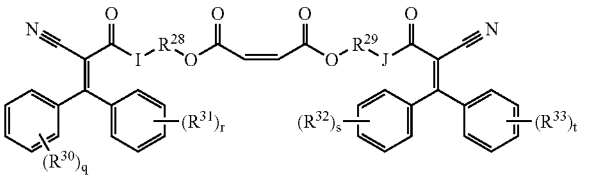

wherein I and J are the same or different and are selected from the group consisting of oxygen, amino and sulfur; $R^{28}$ and $R^{29}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{30}$, $R^{31}$, $R^{32}$ and $R^{33}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and q, r, s and t are each in the range of 0 to 4.

53. The compound of claim 52, wherein $R^{28}$ and $R^{29}$ are selected from the group consisting of $C_2$-$C_{15}$ alkyl.

54. The compound of claim 53, wherein $R^{28}$ and $R^{29}$ are the same and are 3,3-dimethyl propane.

55. The compound of claim 52, wherein I and J are oxygen.

56. A compound of formula (VI):

(VI)

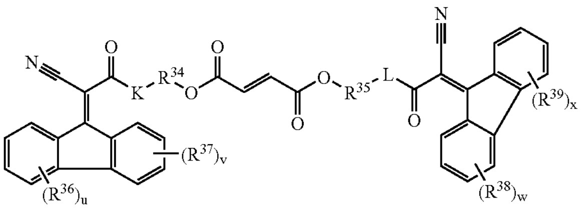

wherein K and L are the same or different and are selected from the group consisting of oxygen, amino and sulfur; $R^{34}$ and $R^{35}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{36}$, $R^{37}$, $R^{38}$ and $R^{39}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and u, v, w and x are each in the range of 0 to 4.

57. The compound of claim 56, wherein $R^{34}$ and $R^{35}$ are selected from the group consisting of $C_2$-$C_{15}$ alkyl.

58. The compound of claim 57, wherein $R^{34}$ and $R^{35}$ are the same and are 3,3-dimethyl propane.

59. The compound of claim 56, wherein K and L are oxygen.

60. A compound of formula (VII):

(VII)

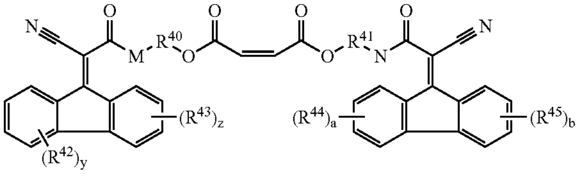

wherein M and N are the same or different and are selected from the group consisting of oxygen, amino and sulfur; $R^{40}$ and $R^{41}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{42}$, $R^{43}$, $R^{44}$ and $R^{45}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and y, z, a and b are each in the range of 0 to 4.

61. The compound of claim 60, wherein $R^{40}$ and $R^{41}$ are selected from the group consisting of $C_2$-$C_{15}$ alkyl.

62. The compound of claim 61, wherein $R^{40}$ and $R^{41}$ are the same and are 3,3-dimethyl propane.

63. The compound of claim 60, wherein M and N are oxygen.

64. A sunscreen composition, comprising a mixture of a photoactive compound and a compound selected from the group consisting of compounds of formula (IV), compounds of formula (V), compounds of formula (VI), compounds of formula (VII), and combinations thereof:

(IV)

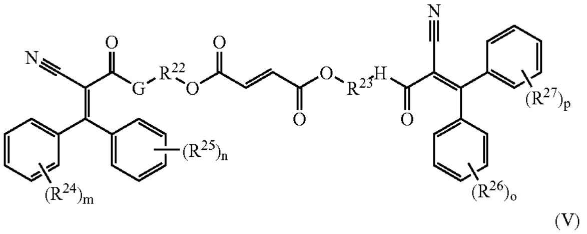

(V)

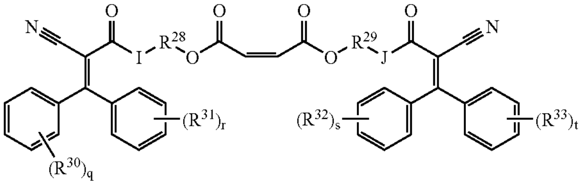

(VI)

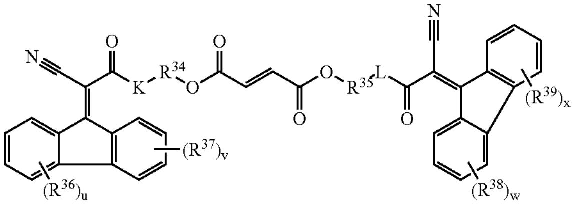

(VII)

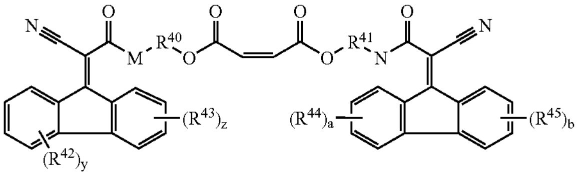

wherein G, H, I, J, K, L, M and N are the same or different and are selected from the group consisting of oxygen, amino and sulfur; $R^{22}$, $R^{23}$, $R^{28}$, $R^{29}$, $R^{34}$, $R^{35}$, $R^{40}$ and $R^{41}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{24}$, $R^{25}$, $R^{26}$, $R^{27}$, $R^{30}$, $R^{31}$, $R^{32}$, $R^{33}$, $R^{36}$, $R^{37}$, $R^{38}$, $R^{39}$, $R^{42}$, $R^{43}$, $R^{44}$ and $R^{45}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and m, n, o, p, q, r, s, t, u, v, w, x, y, z, a and b are each in the range of 0 to 4.

65. The composition of claim 64, wherein $R^{22}$, $R^{23}$, $R^{28}$, $R^{29}$, $R^{34}$, $R^{35}$, $R^{40}$ and $R^{41}$ are selected from the group consisting of $C_2$-$C_{15}$ alkyl.

66. The composition of claim 65, wherein $R^{22}$, $R^{23}$, $R^{28}$, $R^{29}$, $R^{34}$, $R^{35}$, $R^{40}$ and $R^{41}$ are each 3,3-dimethylpropane.

67. The composition of claim 64, wherein G, H, I, J, K, L, M and N are each oxygen.

68. The composition of claim 64, comprising a dibenzoylmethane derivative.

69. A method of photostabilizing a sunscreen composition comprising a photoactive compound, said method comprising the step of, adding to said sunscreen composition a photostabilizing amount of a compound selected from the group consisting of compounds of formula (IV), compounds of formula (V), compounds of formula (VI), compounds of formula (VII), and combinations thereof:

(IV)

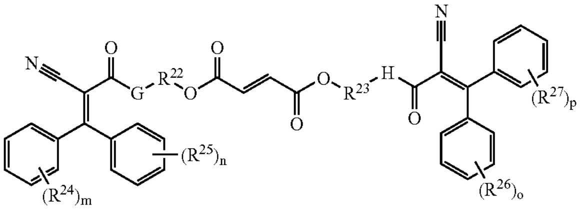

(V)

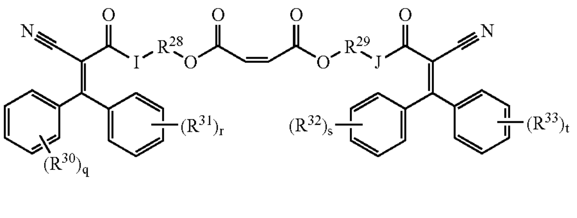

(VI)

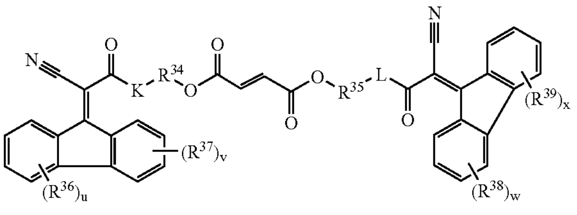

-continued (VII)

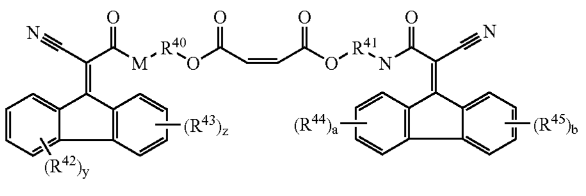

wherein G, H, I, J, K, L, M and N are the same or different and are selected from the group consisting of oxygen, amino and sulfur; $R^{22}$, $R^{23}$, $R^{28}$, $R^{29}$, $R^{34}$, $R^{35}$, $R^{40}$ and $R^{41}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{24}$, $R^{25}$, $R^{26}$, $R^{27}$, $R^{30}$, $R^{31}$, $R^{32}$, $R^{33}$, $R^{36}$, $R^{37}$, $R^{38}$, $R^{39}$, $R^{42}$, $R^{43}$, $R^{44}$ and $R^{45}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and m, n, o, p, q, r, s, t, u, v, w, x, y, z, a and b are each in the range of 0 to 4.

70. The method of claim 69, wherein $R^{22}$, $R^{23}$, $R^{28}$, $R^{29}$, $R^{34}$, $R^{35}$, $R^{40}$ and $R^{41}$ are selected from the group consisting of $C_2$-$C_{15}$ alkyl.

71. The method of claim 70, wherein $R^{22}$, $R^{23}$, $R^{28}$, $R^{29}$, $R^{34}$, $R^{35}$, $R^{40}$ and $R^{41}$ are each 3,3-dimethylpropane.

72. The method of claim 69, wherein G, H, I, J, K, L, M and N are each oxygen.

73. A method of photostabilizing a dibenzoylmethane derivative, said method comprising the step of, adding to said dibenzoylmethane derivative a photostabilizing amount of a compound selected from the group consisting of compounds of formula (IV), compounds of formula (V), compounds of formula (VI), compounds of formula (VII), and combinations thereof:

(IV)

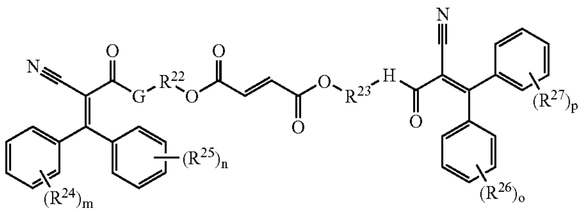

(V)

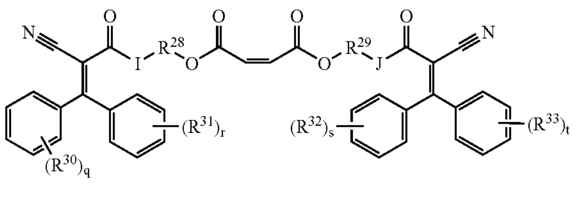

-continued (VI)

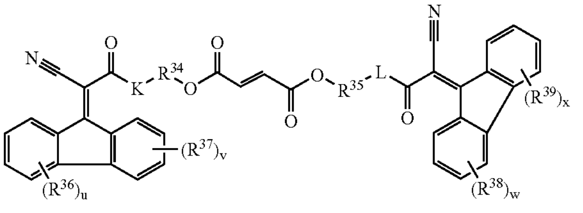

(VII)

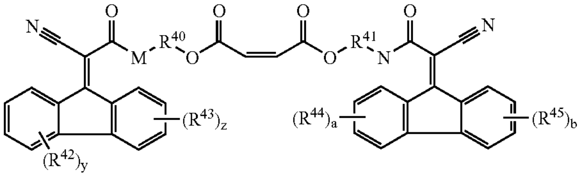

wherein G, H, I, J, K, L, M and N are the same or different and are selected from the group consisting of oxygen, amino and sulfur; $R^{22}$, $R^{23}$, $R^{28}$, $R^{29}$, $R^{34}$, $R^{35}$, $R^{40}$ and $R^{41}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{24}$, $R^{25}$, $R^{26}$, $R^{27}$, $R^{30}$, $R^{31}$, $R^{32}$, $R^{33}$, $R^{36}$, $R^{37}$, $R^{38}$, $R^{39}$, $R^{42}$, $R^{43}$, $R^{44}$ and $R^{45}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and m, n, o, p, q, r, s, t, u, v, w, x, y, z, a and b are each in the range of 0 to 4.

74. The method of claim 73, wherein $R^{22}$, $R^{23}$, $R^{28}$, $R^{29}$, $R^{34}$, $R^{35}$, $R^{40}$ and $R^{41}$ are selected from the group consisting of $C_2$-$C_{15}$ alkyl.

75. The method of claim 74, wherein $R^{22}$, $R^{23}$, $R^{28}$, $R^{29}$, $R^{34}$, $R^{35}$, $R^{40}$ and $R^{41}$ are each 3,3-dimethylpropane.

76. The method of claim 73, wherein G, H, I, J, K, L, M and N are each oxygen.

77. A method of protecting human skin from ultraviolet radiation comprising topically applying to said skin, in a cosmetically acceptable carrier, a compound selected from the group consisting of compounds of formula (IV), compounds of formula (V), compounds of formula (VI), compounds of formula (VII), and combinations thereof:

(IV)

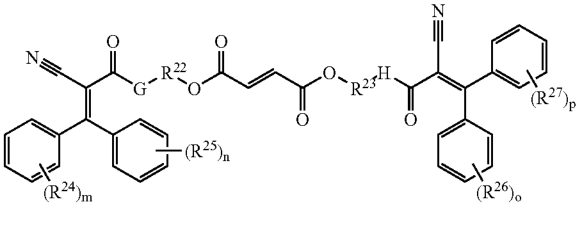

-continued (V)

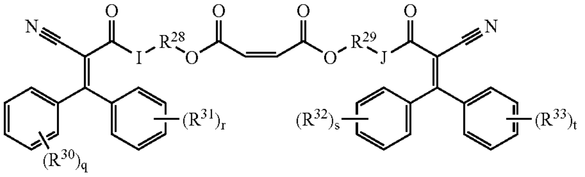

(VI)

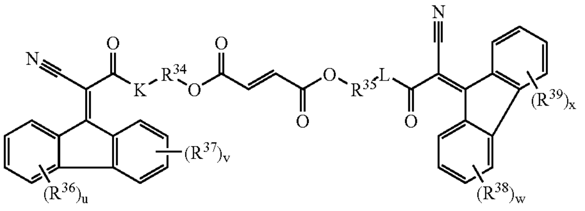

(VII)

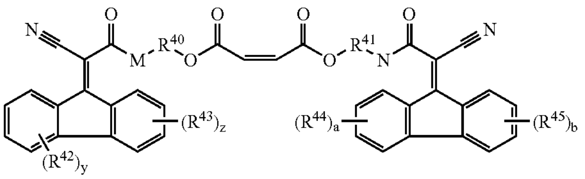

wherein G, H, I, J, K, L, M and N are the same or different and are selected from the group consisting of oxygen, amino and sulfur; $R^{22}$, $R^{23}$, $R^{28}$, $R^{29}$, $R^{34}$, $R^{35}$, $R^{40}$ and $R^{41}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^{24}$, $R^{25}$, $R^{26}$, $R^{27}$, $R^{30}$, $R^{31}$, $R^{32}$, $R^{33}$, $R^{36}$, $R^{37}$, $R^{38}$, $R^{39}$, $R^{42}$, $R^{43}$, $R^{44}$ and $R^{45}$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_2$-$C_{30}$ substituted alkylene, $C_2$-$C_{30}$ substituted alkyne, aryl, substituted aryl, heteroaryl, heterocycloalkyl, substituted heteroaryl, substituted heterocycloalkyl, hydroxyl, ester, carboxy, cyano, amino, amido, sulfur and halo; and m, n, o, p, q, r, s, t, u, v, w, x, y, z, a and b are each in the range of 0 to 4.

78. The method of claim 77, wherein $R^{22}$, $R^{23}$, $R^{28}$, $R^{29}$, $R^{34}$, $R^{35}$, $R^{40}$ and $R^{41}$ are selected from the group consisting of $C_2$-$C_{15}$ alkyl.

79. The method of claim 77, wherein $R^{22}$, $R^{23}$, $R^{28}$, $R^{29}$, $R^{34}$, $R^{35}$, $R^{40}$ and $R^{41}$ are each 3,3-dimethylpropane.

80. The method of claim 77, wherein G, H, I, J, K, L, M and N are each oxygen.

* * * * *